United States Patent
Annan et al.

(10) Patent No.: US 10,247,680 B2
(45) Date of Patent: Apr. 2, 2019

(54) SYSTEM AND METHOD FOR MEASUREMENT OF MATERIAL PROPERTY USING VARIABLE REFLECTOR

(71) Applicant: Sensors & Software Inc., Mississauga (CA)

(72) Inventors: Peter Annan, Mississauga (CA); David Redman, Georgetown (CA)

(73) Assignee: SENSORS & SOFTWARE INC., Mississauga (CA)

( * ) Notice: Subject to any disclaimer, the term of this patent is extended or adjusted under 35 U.S.C. 154(b) by 229 days.

(21) Appl. No.: 14/392,282

(22) PCT Filed: Jun. 27, 2014

(86) PCT No.: PCT/CA2014/050618
§ 371 (c)(1),
(2) Date: Dec. 24, 2015

(87) PCT Pub. No.: WO2014/205582
PCT Pub. Date: Dec. 31, 2014

(65) Prior Publication Data
US 2016/0187266 A1    Jun. 30, 2016

Related U.S. Application Data

(60) Provisional application No. 61/840,742, filed on Jun. 28, 2013, provisional application No. 61/840,709, filed on Jun. 28, 2013.

(51) Int. Cl.
*G01N 22/04*    (2006.01)
*G01N 22/00*    (2006.01)
(Continued)

(52) U.S. Cl.
CPC .............. *G01N 22/04* (2013.01); *G01N 22/00* (2013.01); *G01N 33/246* (2013.01);
(Continued)

(58) Field of Classification Search
CPC ...... G01N 22/04; G01N 33/246; G01N 22/00; G01N 33/46; G01N 33/383; G01S 7/41
(Continued)

(56) References Cited

U.S. PATENT DOCUMENTS 5,822,685 A    10/1998    Forster
6,243,012 B1    6/2001    Shober et al.
(Continued)

FOREIGN PATENT DOCUMENTS

| CA | 2007300 | 7/1990 |
|---|---|---|
| EP | 0952444 | 10/1999 |
| WO | 2004068081 | 8/2004 |

OTHER PUBLICATIONS

Kraus, "Antennas", McGraw Hill, 1988, ISBN 0-07-0354422-7.
(Continued)

*Primary Examiner* — Giovanni Astacio-Oquendo
(74) *Attorney, Agent, or Firm* — Bereskin & Parr LLP/S.E.N.C.R.L., S.R.L.

(57) ABSTRACT

A system and method for measuring a material includes at least one transmitter for transmitting a first signal and a second signal. A variable reflector reflects a portion of the first signal at a first reflecting property to produce a first reflected signal, the portion of the first signal having traveled through the material. The variable reflector also reflects a portion of the second signal at a second reflecting property to produce a second reflected signal, the portion of the second signal having traveled through the material. A receiver receives the first received signal and the second received signal, the first received signal includes the first reflected signal having traveled through the material and the second received signal includes the second reflected signal having traveled through the material. The first reflected signal and the second reflected signal providing an indication of at least one property of the material. The at least one
(Continued)

property includes permittivity, attenuation, anisotropy, and frequency dependency of the material.

22 Claims, 18 Drawing Sheets

(51) Int. Cl.
  *G01N 33/24* (2006.01)
  *G01S 7/41* (2006.01)
  *G01N 33/38* (2006.01)
  *G01N 33/46* (2006.01)

(52) U.S. Cl.
  CPC ........... *G01N 33/383* (2013.01); *G01N 33/46* (2013.01); *G01S 7/41* (2013.01)

(58) Field of Classification Search
  USPC .................. 324/640, 639, 637, 629, 600
  See application file for complete search history.

(56) References Cited

U.S. PATENT DOCUMENTS

| | | | |
|---|---|---|---|
| 6,617,972 B2* | 9/2003 | Takarada | G08B 21/0484 324/538 |
| 8,779,729 B2* | 7/2014 | Shiraishi | G01R 31/3606 320/155 |
| 2004/0119984 A1* | 6/2004 | Andreev | G01B 11/00 356/495 |
| 2009/0273506 A1 | 11/2009 | Delin | |
| 2010/0315642 A1* | 12/2010 | Chow | G01J 3/433 356/432 |
| 2012/0007768 A1 | 1/2012 | Hemmendorff | |
| 2012/0098518 A1* | 4/2012 | Unagami | G01R 22/066 324/74 |
| 2012/0300207 A1 | 11/2012 | Baer | |
| 2015/0233534 A1* | 8/2015 | Kaiser | G01J 1/0414 250/234 |
| 2017/0023484 A1* | 1/2017 | Wang | G01N 21/718 |

OTHER PUBLICATIONS

Finkenzeller, "RFID handbook: Radio-frequency identification fundamentals and applications", John Wiley (New York), 1999, ISBN 0471988510.
Schofthaler et al., "Sensitivity and transient response of microwave reflection measurements", J. Appl. Phys. 77 (7), pp. 3162-3173, Apr. 1, 1995.
Supplementary Partial European Search Report, European Application No. 14816947.7, dated Apr. 18, 2017.
Matsuoka et al., "Anisotropic radio-wave scattering from englacial water regimes, Myrdalsjokull, Iceland", Journal of Glaciology, vol. 53, No. 182, pp. 473-478, Dec. 31, 2007.
Martinez et al., "Modeling Dielectric-constant values of Geologic Materials: An Aid to Ground-Penetrating Radar Data Collection and Interpretation", Current Research in Earth Sciences, Bulletin 247, part 1, pp. 1-16, Dec. 3, 2001.
Topp et al., "Electromagnetic determination of soil water content: Measurements in coaxial transmission lines", Water Resour. Res. 16:574-582.
Babakhani et al., "Transmitter Architectures Based on Near-Field Direct Antenna Modulation", IEEE Journal of Solid-State Circuits, 2008, vol. 43, No. 12.
Brunfeldt et al., Active Reflector for Radar Calibration Geoscience and Remote Sensing, IEEE Transaction, 1984, GE-22, Issue:2.
Bracht et al., "Using an impedance modulated reflector for passive communication", Antennas and Propagation Society International Symposium, 1997, IEEE, 1997 Digest, v2.

\* cited by examiner

SYSTEM AND METHOD FOR MEASUREMENT OF MATERIAL PROPERTY USING VARIABLE REFLECTOR

RELATED PATENT APPLICATIONS

This application is a National Stage (371) of International Application No. PCT/CA2014/050618 filed Jun. 27, 2014, which claims the benefit of U.S. Provisional Application No. 61/840,709, filed Jun. 28, 2013, and also claims the benefit of U.S. Provisional Application No. 61/840,742, filed Jun. 28, 2013, the disclosures of which are both incorporated by reference herein in their entirety.

This application claims the benefit of U.S. Provisional Application No. 61/840,709, filed Jun. 28, 2013, and also claims the benefit of U.S. Provisional Application No. 61/840,742, filed Jun. 28, 2013, the disclosures of which are both incorporated by reference herein in their entirety.

FIELD

The present disclosure relates generally to the field of measurement of at least one property of a material using reflectometry. More specifically, the embodiments of the present disclosure relate to measurement of at least one physical property of a material using a variable reflector that can be external to the material or embedded in the material.

INTRODUCTION

Numerous methods have been used in the study of geologic materials to measure material properties of representative bulk samples. One topic area of interest is the study of geologic materials to indirectly determine water content, such as described by Topp, G. C., J. L. Davis, and A. P. Annan, 1980: Electromagnetic determination of soil water content: Measurements in coaxial transmission lines. Water Resour. Res. 16:574-582. A time-domain reflectometry method is used to measure water content in soils via sensing electrical properties (dielectric permittivity) from the electromagnetic wave velocity at radio-wave frequencies.

Many publications address the use of ultra-wide band ground penetrating radar to exploit various reflector characteristics to extract travel-time and transmission amplitude variations in a material. Physical and empirical relationships are then used to estimate bulk dielectric constant (permittivity) and attenuation. Relationships, such as disclosed in Topp et al, are used to further indicate related physical properties such as water content, density, porosity and others.

An electromagnetic field impinging on conductive wire creates a current flowing through the conductive wire, which then creates a secondary electromagnetic field in the space surrounding the wire. This is often known as scattering. Wire antennas or scatters apply this phenomenon. For example, Kraus [1] provides a description of this phenomenon.

The response of a wire to an incident electromagnetic field can be complex and is dependent on the electrical properties of the wire, the geometrical shape of the wire, and properties of the environment surrounding the wire.

Examples of application of this phenomenon include repeaters, which receive an electromagnetic radio wave signal and then retransmit, amplify or somehow modify and resend the signal, a variety of target detection encoding and detecting methods such as RFID, and methods of calibrating radar systems and scatterometers. Examples of these can be found in references [2]-[7].

SUMMARY

The present disclosure provides in a first aspect a system for measuring a material. The system includes at least one transmitter for transmitting at least a first signal and a second signal; at least one variable reflector for reflecting a portion of the first signal at a first reflecting property to produce a first reflected signal, the portion of the first signal having traveled through the material, and for reflecting a portion of the second signal at a second reflecting property to produce a second reflected signal, the portion of the second signal having traveled through the material; at least one receiver for receiving at least a first received signal and at least a second received signal, the first received signal comprising the first reflected signal having traveled through the material and the second received signal comprising the second reflected signal having traveled through the material, the first reflected signal and the second reflected signal providing an indication of at least one property of the material.

The present disclosure presents in another aspect a method for measuring a material. The method includes the steps of transmitting at least a first signal into the material and a second signal into the material; controlling at least one reflector to reflect a portion of the first signal at a first reflecting property to produce a first reflected signal, the portion of the first signal having traveled through the material; controlling the at least one reflector to reflect a portion of the second signal at a second reflecting property to produce a second reflected signal, the portion of the second signal having traveled through the material; receiving at least a first received signal and at least a second received signal, the first received signal comprising the first reflected signal having traveled through the material and the second received signal comprising the second reflected signal having traveled through the material, the first reflected signal and the second reflected signal providing an indication of at least one property of the material.

The present disclosure presents in yet another aspect a kit for measuring a material. The kit includes at least one transmitter for transmitting at least a first signal and a second signal, at least one variable reflector for reflecting a signal at a first reflecting property and reflecting a signal at a second reflecting property, a receiver for receiving at least a first received signal and at least a second received signal, and a non-transitory computer-readable medium upon which a plurality of instructions are stored. The instructions are for controlling at least one transmitter to transmit the first signal, controlling at least one transmitter to transmit the second signal, controlling at least one variable reflector to adjust the reflecting property of the reflected between the first reflecting property and the second reflecting property, and isolating a first reflected signal of the first received signal and a second reflected signal of the second received signal.

The present disclosure provides in yet another aspect a variable reflector having a plurality of elongated conductive elements interconnected by at least one variable electrical impedance junction element, a variation of the impedance of the junction element varying a scattering electromagnetic field scattering from the plurality of interconnected elongated conductive elements when energized.

The present disclosure provides in yet another aspect a variable reflector having a plurality of elongated conductive elements for scattering electromagnetic field therefrom when energized; and a motor for rotating the plurality of elongated conductive elements.

The present disclosure provides in yet another aspect a variable reflector having a plurality of elongated conductive elements interconnected by at least one variable electrical impedance junction element, a variation of the impedance of the junction element varying a scattering electromagnetic field scattering from the plurality of interconnected elongated conductive elements when energized. A first set of the plurality of elongated conductive elements is interconnected by a first set of the at least one junction element and is supported on a first electromagnetically permeable support layer and has a first orientation and a second set of the plurality of elongated conductive elements is interconnected by a second set of the at least one junction element and is supported on a second support layer and has a second orientation that is different from the first orientation.

DRAWINGS

A detailed description of various exemplary embodiments is provided herein below with reference to the following drawings, by way of example only, and in which.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any ways, but rather as merely describing the implementation of the various embodiments described herein.

Various known methods of using reflectometry measure properties of a material based on the reflection of signals from the surface of the material itself. By contrast, various systems, apparatus, methods and kits described herein do not depend on the direct reflective properties of the material, but instead use signal transmission through the material with reflection from at least one variable or modulated reflector to determine at least one property of the material.

"Sample material" herein refers to a physical material under test and for which at least one property of the material is not known and is to be determined according to systems, apparatus, methods and kits described herein. At least one property of the sample material includes, but is not limited to, signal velocity, attenuation, directivity, dielectric permittivity, water content, degree of water hydration.

Figure 1:
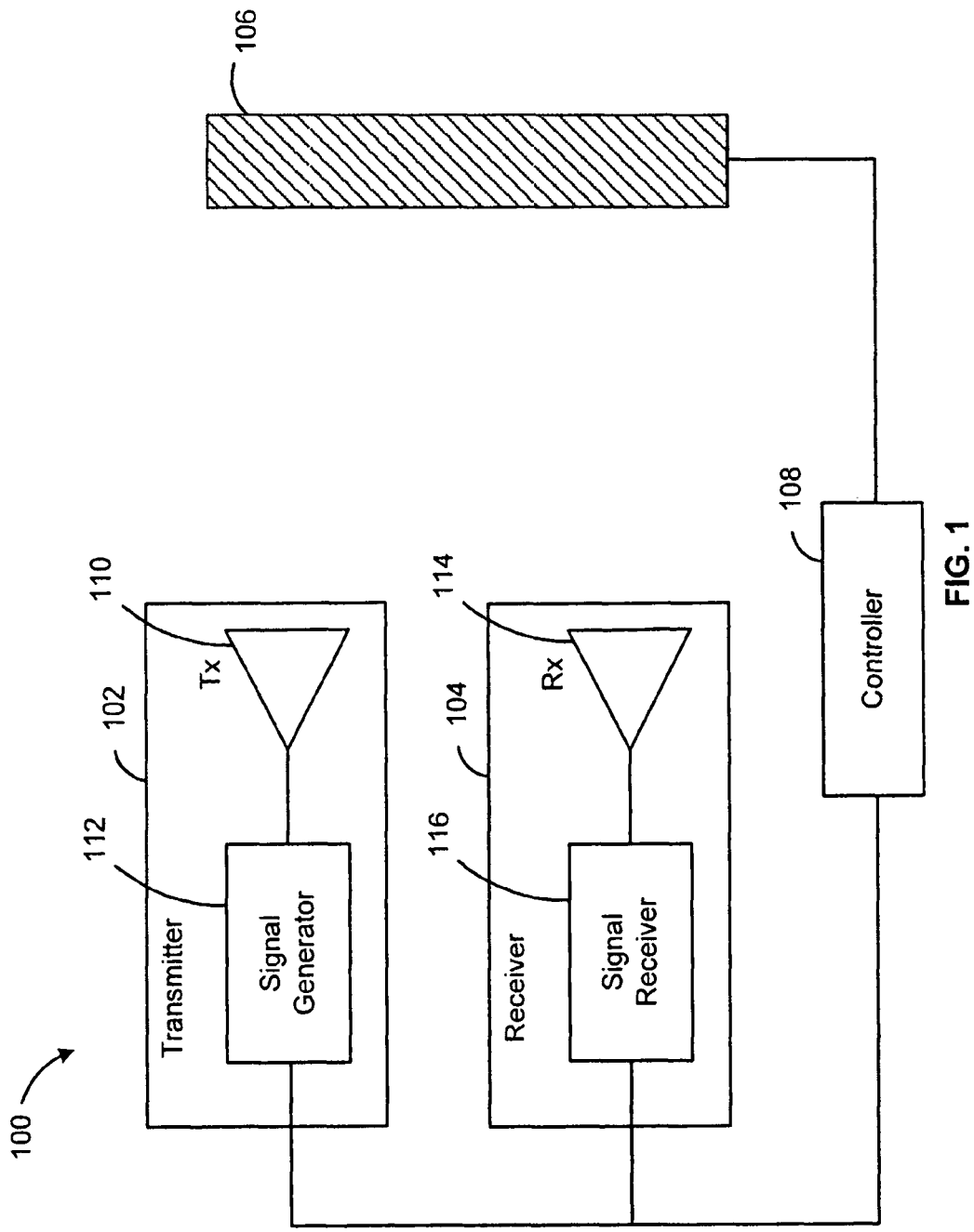
FIG. 1 is a schematic diagram of a system for measuring a property of a material according to various exemplary embodiments.

Referring to FIG. 1, therein illustrated is a schematic diagram according to various embodiments of a measurement system 100 for measuring at least one property of a sample material. The measurement system 100 includes a transmitter 102, receiver 104, at least one variable reflector 106.

The measurement system 100 can further include a controller 108. Alternatively, an external controller 108 can be connected to the measurement system 100 to communicate with various components of the measurement system 100.

The measurement system 100 can further include a signal processor for processing signals received by the receiver 104. In some cases, the signal processor may be embedded with the controller 108. Alternatively, received signals can be sent to an external signal processor for analysis.

Either one, or both, of the controller 108 and the signal processor may be implemented in hardware or software, or a combination of both. It may be implemented on a programmable processing device, such as a microprocessor or microcontroller, Central Processing Unit (CPU), Digital Signal Processor (DSP), Field Programmable Gate Array (FPGA), general purpose processor, and the like. In some embodiments, the programmable processing device can be coupled to program memory, which stores instructions used to program the programmable processing device to execute the controller. The program memory can include non-transitory storage media, both volatile and non-volatile, including but not limited to, random access memory (RAM), dynamic random access memory (DRAM), static random access memory (SRAM), read-only memory (ROM), programmable read-only memory (PROM), erasable programmable read-only memory (EPROM), electrically erasable programmable read-only memory (EEPROM), flash memory, magnetic media, and optical media.

The transmitter 102 includes at least one transmitting element 110 and signal generator unit 112. The signal generator unit 112 can create at least one signal that can be then transmitted from the transmitting element 110. For example, transmitting of a signal is controlled by control signals received from the controller 108. For example, the type of signal (ex: frequency, amplitude) and the timing of the signal to be transmitted can be controlled by the controller 108. For example, the signal generator unit 112 can include a digital-to-analog convertor for converting a digital signal received from the controller 108 into an analog signal to be transmitted by the transmitting element 110.

The transmitting element 110 can have a defined directivity to minimize spurious signals. For example, the transmitting element 110 can have a directivity such that a significant portion of the transmitted signal travels through the sample material and is reflected by the variable reflector 106.

For example, the transmitting element 110 can be an antenna capable of emitting radio frequency signals generated by the signal generator unit 112. However, it will be understood that other types of suitable transmitting elements 110 can be used for transmitting other types of signals generated by the signal generator unit 112. For example, transmitting element 110 can be a speaker for emitting acoustic signals generated by the signal generator unit 112. Alternatively, the transmitting element 110 can emit various types of elastic waves. The transmitting element 110 can be other suitable transducer element for emitting signal waves.

The receiver 104 includes at least one receiving element 114 for receiving signals and signal receiver unit 116. For example, the signal receiver unit 116 includes an analog-to-digital converter for converting a received analog signal to a digital signal. For example, the signal receiver unit 116 is in communication with the controller 108 or signal processor and can send received signals to the controller 108 or signal processor for analysis. Alternatively, received signals can be partially or completely analyzed by the signal receiver unit 116. The type of the receiving element 114 can be chosen based on the type of signals emitted from the transmitting element 110. For example, the receiving element 114 can be a receiving antenna for receiving radio frequency waves, or a microphone for receiving acoustic signals, or another type of element for receiving other types of waves.

The variable reflector 106 can reflect signals sent from the transmitting element 110. The variable reflector 106 can be characterized according to at least one reflecting property. "Reflecting property", as used herein refers to a property of the variable reflector 106 that can be characterized by the manner in which the variable reflector 106 changes an incident signal when reflecting that signal. For example, depending on the nature of the signal, one or more reflecting properties can be selected for the variable reflector 106. For example, where the signal sent from the transmitting element 110 is characterized by a vector wavefield, the reflecting property can be reflectivity amplitude of the variable reflector 106, which can be independent of the incident excitation vector direction of the vector wavefield. Alternatively, the reflecting property can be the reflectivity amplitude of the variable reflector 106 that is dependent on the incident excitation vector direction (often referred to as field polarization) or anisotropy. For example, the reflectivity of the variable reflector 106 can also depend on excitation frequency. In some embodiments, the selected reflectivity of the variable reflector 106 can depend on a combination of the above.

For example, as shown in FIG. 1, the variable reflector 106 is connected to the controller 108 via one or more control lines and the selection of the reflecting property of the variable reflector 106 can be controlled by the controller 108. Accordingly, the timing of the selection of the reflecting property of the variable reflector 106 can be synchronized with the timing of the transmission of signals from the transmitting element 110. Alternatively, the variable reflector 106 is not in communication with the controller 108, and the adjusting of the reflecting property of the variable reflector 106 is made independently of the timing of the transmissions of the signal from the transmitting element 110.

According to various exemplary embodiments, the transmitting element 110 is mountable near or onto a surface of the sample material such that along at least one path, signals transmitted by the transmitting element 110 substantially only travel through the sample material. In other exemplary embodiments, transmitting element 110 can be positioned within the sample material, such as embedded within the sample material.

According to various exemplary embodiments, the receiving element 114 is mountable near or onto a surface of the sample material such that along at least one path, signals received by the receiving element 114 will substantially only have traveled through the sample material. In other embodiments, the receiving element 114 can be positioned within the sample material, such as embedded within the sample material.

According to various exemplary embodiments, the transmitter 102 and the receiver 104 are in one-way or mutual communication. For example, the transmitter 102 can communicate to the receiver 104 the time at which the transmitter 102 transmits a signal. Alternatively, the transmitter 102 and the receiver 104 are controlled by the controller 108. For example, the controller 108 can control when the transmitter 102 transmits a signal and when the receiver 104 begins receiving signals. In other exemplary embodiments, both the transmitter 102 and the receiver 104 have internal clocks, and synchronization between the receiver 104 and the transmitter 102 can be achieved through use of the internal clocks.

According to various exemplary embodiments, the variable reflector 106 is decoupled from the transmitter 102 and the receiver 104. The variable reflector 106 can be out of communication with the transmitter 102, the receiver 104 and the controller 108. For example, each of the transmitter 102 and the controller 108 can have internal clocks and synchronization between the transmitter 102 and the controller 108 can be achieved through use of the internal clocks. For example, the time of transmitting a signal from the transmitter 102 and the time for adjusting the reflecting property of the variable reflector 106 can be synchronized. Alternatively, the transmitter 102 and the variable reflector 106 are not in synchronization and the adjustment of the reflecting property of the variable reflector 106 is carried out independently of the timing of the transmission of a signal from the transmitter 102.

According to various exemplary embodiments, the variable reflector 106 is mountable near or onto a surface of the sample material such that along at least one path, signals reflected by the variable reflector 106 will substantially only travel though the sample material.

According to various exemplary embodiments, the measurement system 100 further includes a mount. For example, the mount is a container for holding the sample material. Alternatively, the mount can be used to mount components of the measurement system 100 onto the surface of a sample material. The mount can be formed of a material that is transparent at a range of frequencies corresponding to the range at which signals are transmitted from the transmitting element 110. For example, the transmitting element 110 can be attached to the mount such that during measurement operation, the transmitting element 110 is positioned near or onto to the surface of the sample material and that along at least one path, signals transmitted by the transmitting element 110 substantially only travels through the sample material. For example, the receiving element 112 can be attached to the mount such that during measurement operation, the receiving element 114 is positioned near or onto the surface of the sample material and that along at least one path, signals received by the receiving element 116 will substantially only have traveled through the sample material. For example, the variable reflector 106 can be attached to the mount such that during measurement operation, the variable reflector 106 is positioned close to the surface of the sample material and that along at least one path, signals reflected by the variable reflector 106 will substantially only travel though the sample material.

Figure 2:
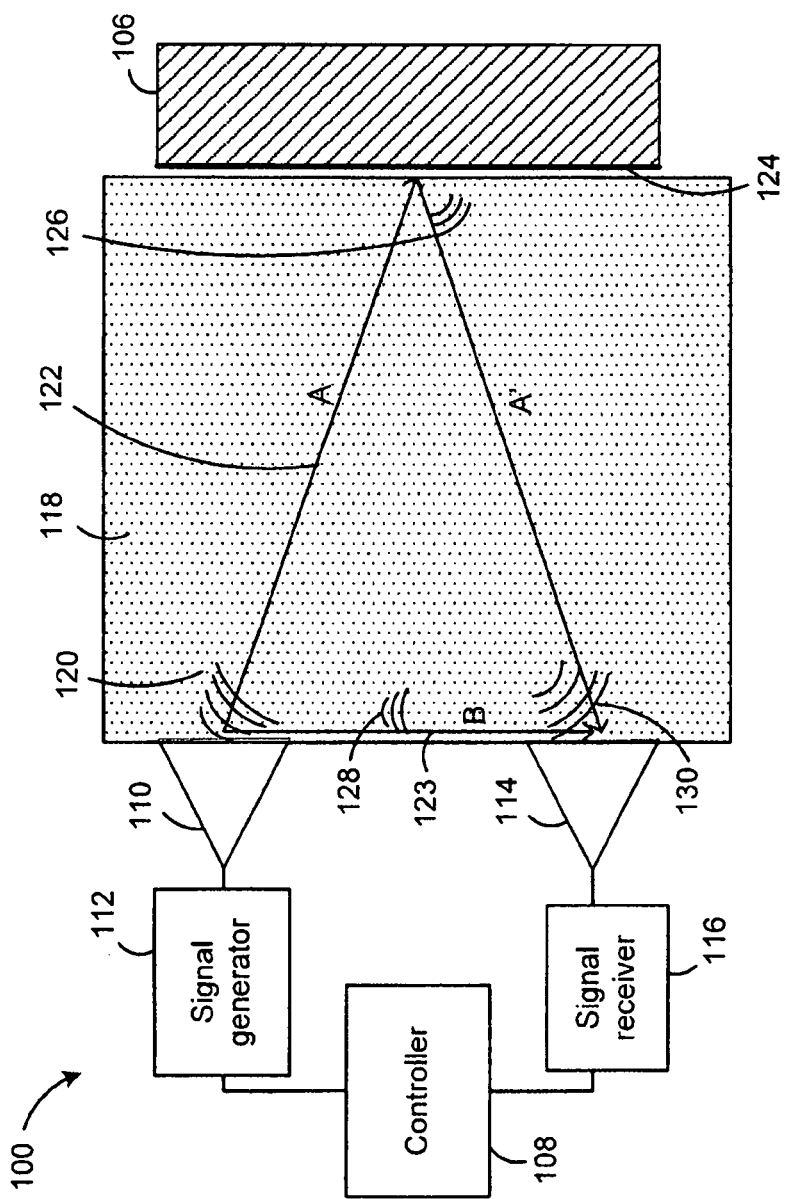
FIG. 2 is a plan view of the measurement system in operation according to one exemplary embodiment.

Referring now to FIG. 2, therein illustrated is a plan view of the measurement system 100 in operation for measuring at least one property of a sample material 118 according to one exemplary embodiment. A transmitting element 110 of the transmitter 102 is mounted near or onto a surface of the sample material 118. A receiving element 114 of the receiver 104 is also mounted near or onto the surface of the sample material 118 and is spaced apart from the transmitting element 110. A transmitted signal 120 is transmitted from the transmitter 102. The transmitted signal 120 can be modeled as traveling over two signal paths between the transmitting element 110 and the receiving element 114. A portion of the transmitted signal 120 travels over a reflected signal path 122 defined by vectors A and A'. Over the reflected signal path 122, the portion of the transmitted signal 120 propagates through the sample 118 material along the vector A to reach a reflecting surface 124 of the variable reflector 106. The portion of the transmitted signal 120 is reflected by the variable reflector 106 and a reflected signal 126 is produced. The reflected signal 126 then propagates through the sample material 118 along the vector A' to reach the receiving element 114 of the receiver 104.

Another portion of the transmitted signal 120 travels over an unreflected signal path 123 defined by vector B. Over the unreflected signal path 123, the portion of the transmitted signal 120 is not reflected by the variable reflector 106. This portion of the transmitted signal 120 is represented as an unreflected signal 128. The unreflected signal 128 propagates through the sample material 118 or outside of the sample material 118 along the unreflected signal path 123 to reach the receiving element 114 of the receiver 102.

It will be appreciated that a received signal 130 received at the receiving element 114 by the receiver 104 includes the unreflected signal 128, corresponding to a portion of the transmitted signal 120 that is not reflected by variable reflector 106, and includes the reflected signal 126, corresponding to a portion of the transmitted signal 120 that is reflected by the variable reflector 106.

It will be understood that the reflected signal path 122 defined by vectors A and A' and the unreflected signal path 123 defined by vector B are illustrated as an exemplary model. In operation, there may be a plurality of additional paths between the transmitter 102 and the receiver 104. However, each of these additional paths can also be modeled in the same manner as the reflected signal path 122 or unreflected signal path 123.

Figure 3:
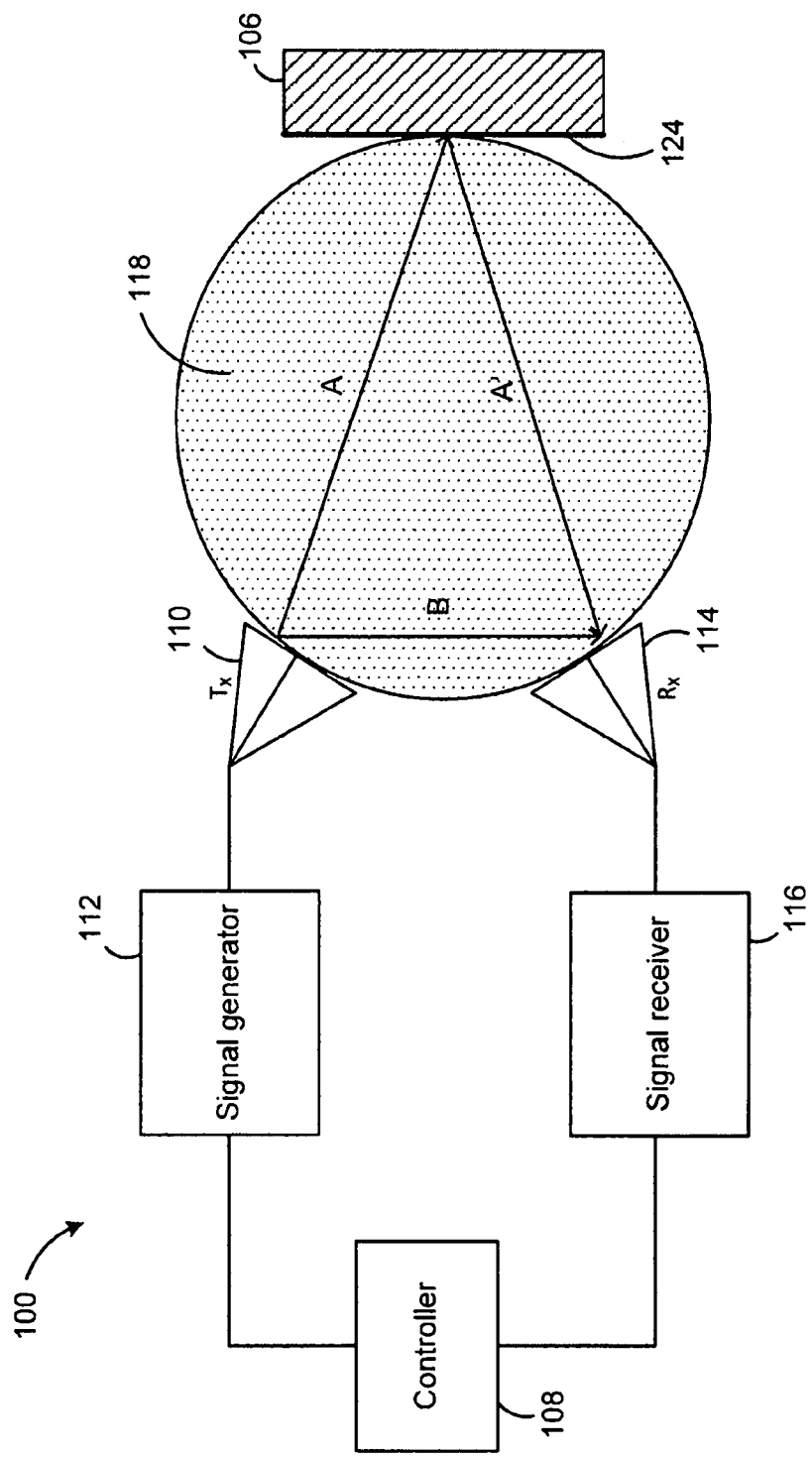
FIG. 3 is a plan view of the measurement system in operation according to another exemplary embodiment.

Referring now to FIG. 3, therein illustrated is a plan view of the measurement system 100 in operation for measuring at least one property of the sample material 118 according to one exemplary embodiment. As shown, the sample material 118 has a substantially circular cross section. For example, the sample material 118 can be a pipe, a pole, mining core, or a natural object such as a tree trunk. However, it will be understood that a sample material 118 having other shapes may be used. The transmitting element 110 is mounted to a surface of the sample material 118. Preferably, the transmitting element 110 forms a tangent with the surface of the sample material 118. The receiving element 114 is mounted near or onto a surface of the sample material 118. Preferably, the receiving element 114 also forms a tangent with the surface of the sample material 118. The variable reflector 106 is mounted such that the reflecting surface 124 of the variable reflector contacts the sample material 118. Preferably, the reflecting surface 124 also forms a tangent with the surface of the sample material 118.

Figure 4:
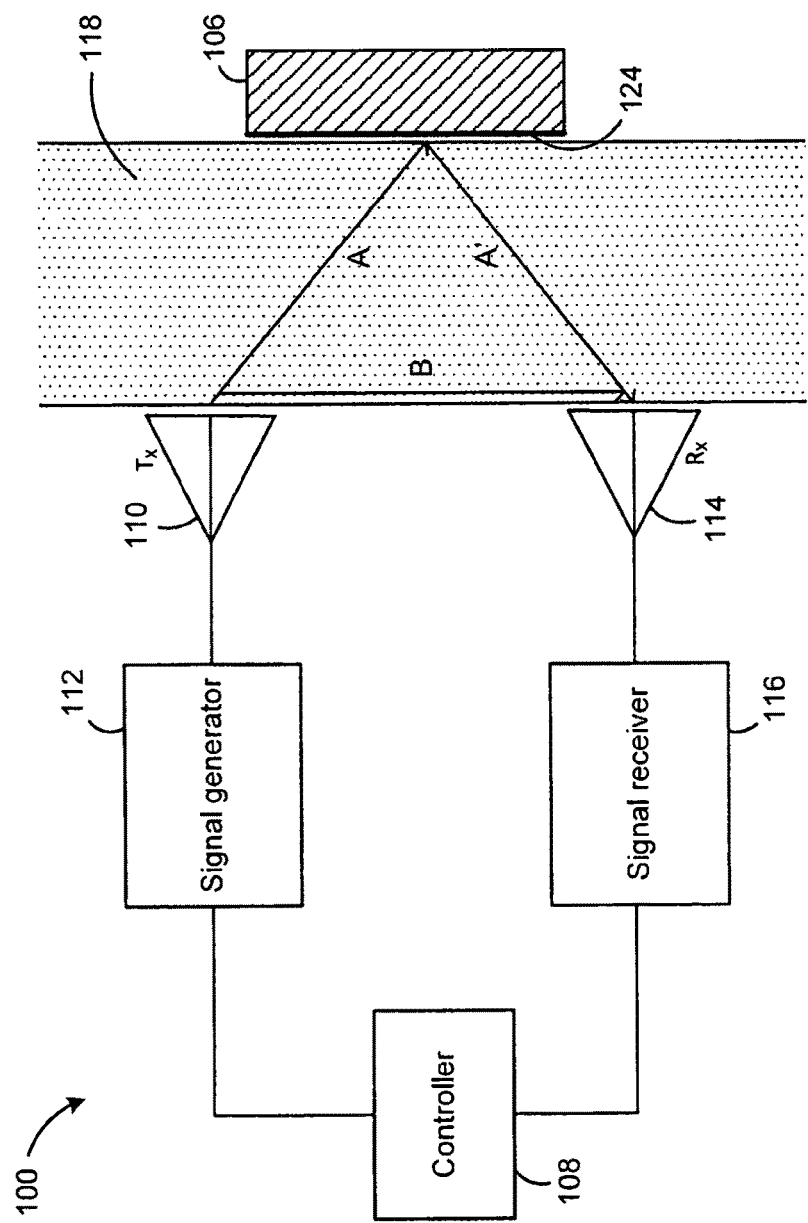
FIG. 4 is a plan view of the measurement system in operation according to yet another exemplary embodiment.

Referring now to FIG. 4, therein illustrated is a plan view of the measurement system 102 in operation for measuring at least one property of the sample material 118 according to one exemplary embodiment. The sample material 118 can be a wall or a slab having a large width and/or length. The transmitting element 110 and receiving element 114 are mounted onto a first surface of the sample material 118. The variable reflector 106 is mounted near or onto a second surface that is opposite the first surface. For example, the variable reflector 106 can be decoupled from the transmitter 102, receiver 104 and/or controller 108. This may be due to the significant size of the sample material 118, which makes it impractical to maintain coupling of the variable reflector 106 with the transmitter 102 and receiver 104 side of the measurement system 100. The variable reflector 106 can also be out of communication with the transmitter 102 and receiver 104 side of the variable reflector 106.

Figure 5:
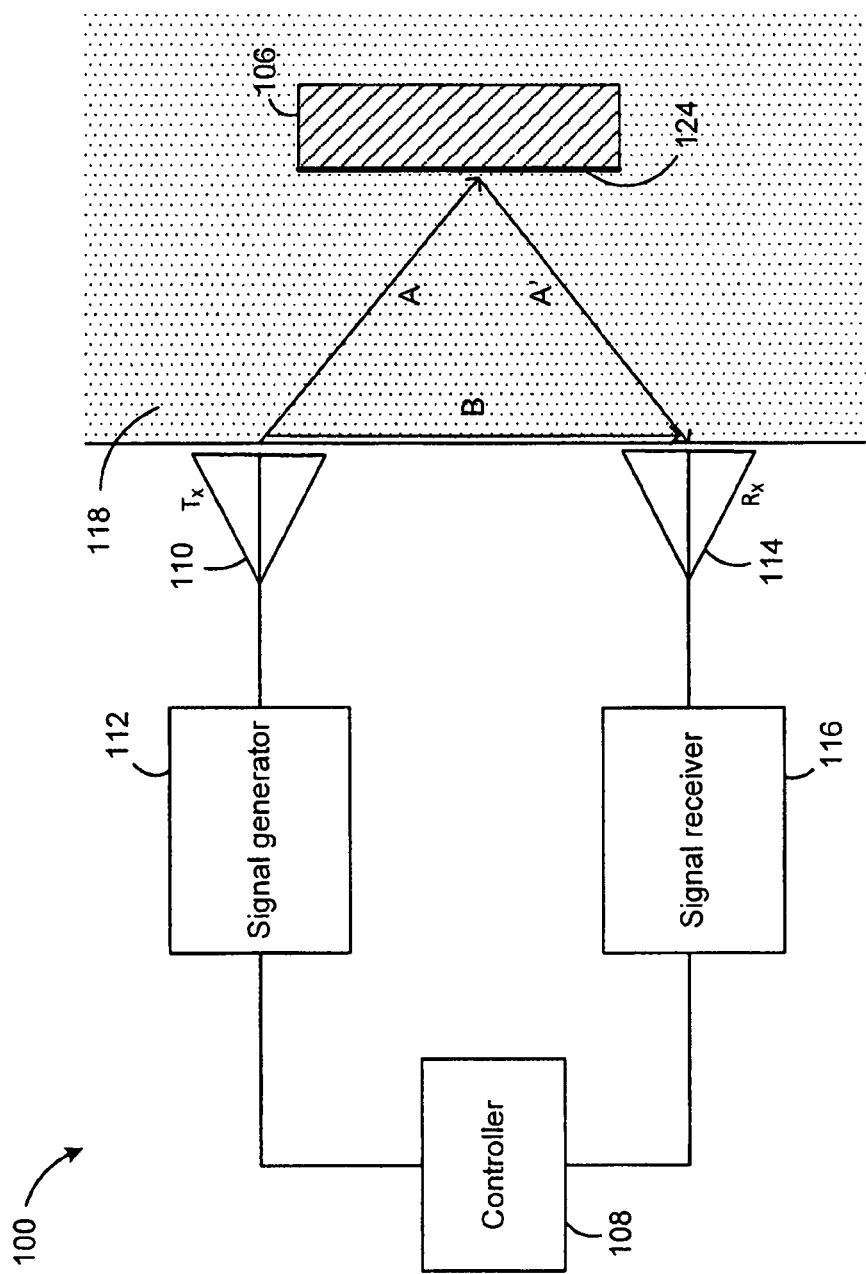
FIG. 5 is a plan view of the measurement system in operation according to yet another exemplary embodiment.

Referring now to FIG. 5, therein illustrated is a plan view of the measurement system 100 in operation for measuring at least one property of the sample material 118 according to one exemplary embodiment. The transmitting element 110 and receiving element 114 are mounted near or onto a surface of the sample material 118. The variable reflector 106 is placed inside the sample material 118. For example, the variable reflector can be embedded inside the sample material 118. For example, the sample material 118 can be a fluid material, and the variable reflector 116 can be inserted into the sample material 118.

Figure 6:
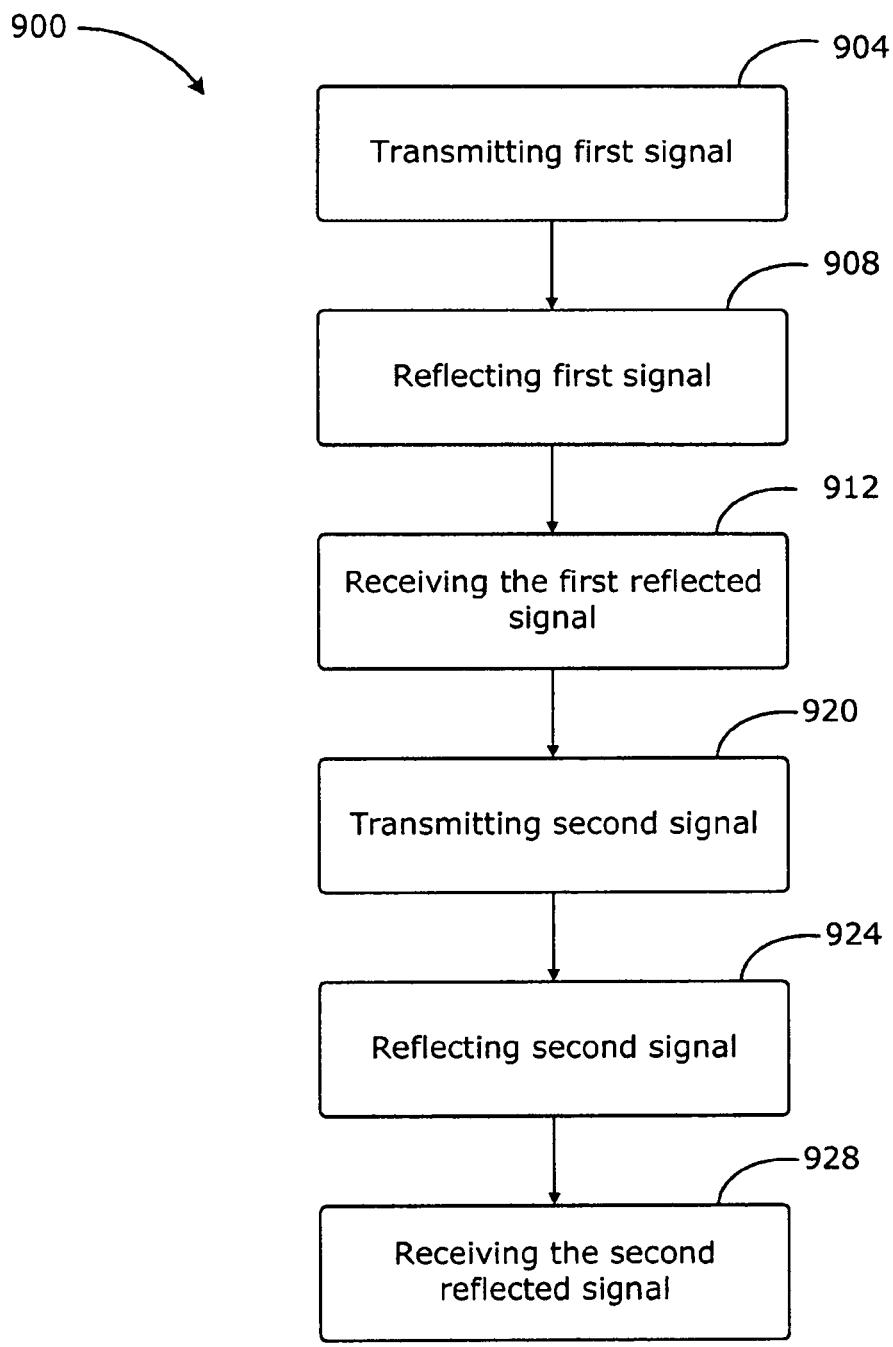
FIG. 6 is a schematic diagram of an exemplary method for measuring a property of a sample material.

Referring now to FIG. 6, therein illustrated is a schematic diagram of an exemplary method 900 for measuring a property of a sample material. For example, the method 900 can be carried out using the measurement system 100 described herein.

At step 904 a first signal 120 is transmitted into the sample material 118. For example, the first signal 120 can be transmitted from the transmitting element 110. For example, the first signal 120 can be a transient signal. For example, the transient signal can be a Gaussian, an error function wavelet or a Ricker wavelet. Alternatively, the first signal 120 can be a periodic signal.

A portion of the first signal 120 transmitted into the sample material 118 travels through the sample material 118 and is reflected by a reflector at step 908 at a first reflecting property. For example, the first signal 120 is reflected by variable reflector 106 that has been adjusted to have the first reflecting property. A first reflected signal 126 is produced from the portion of the first signal 120 being reflected. The first reflected signal 126 continues to propagate through the sample material 118.

At step 912, a first received signal 130 is received. For example, the first received signal 130 is received by the receiving element 114 of receiver 104. The first received signal 130 includes the first reflected signal 126 that traveled through the sample material 118 and also an unreflected portion 128 of the first transmitted signal 120.

Referring back to FIGS. 2-5, a portion of the first signal 120 transmitted into the sample material 118 can be generally modeled as having traveled over the path defined by vector A to reach the reflector 106. After being reflected by the reflector 106, the first reflected signal 126 that is produced can be generally modeled as having traveled over the path denoted by the vector A' to reach the receiver 104. The first reflected signal 126 represents the portion of the first transmitted signal 120 that traveled over the path AA'.

Continuing with FIGS. 2-5, the unreflected portion 128 of the first transmitted signal 128 can be generally modeled as having traveled over the path denoted by the vector B to reach the receiver 104 without being reflected by the variable reflector 106.

At step 920 a second signal 120 is transmitted into the sample material 118. For example, the second signal 120 is also transmitted from the transmitting element 110. For example, the first signal 120 and the second signal 120 have substantially the same characteristics. For example, the first signal 120 and the second signal 120 can be identical. According to various exemplary embodiments, the transmitting of the first signal 120 and the transmitting of the second signal 120 can be spaced apart temporally. For example, the transmitting of the first signal 120 and the transmitting of the second signal 120 can be spaced apart for a duration of time that is greater than the time required to adjust the reflecting property of the variable reflector 106 from a first reflecting property to a second reflecting property. For example, the transmitting of the first signal 120 and the transmitting of the second signal 120 can be spaced apart for a duration of time that is greater than the time required for a first signal 120 to be reflected by a reflector and for the first received signal 130 to be received at the receiving element 114.

A portion of the second signal 120 transmitted into the sample material 118 travels through the material and is reflected by a reflector at step 924 at a second reflecting property. According to various exemplary embodiments, the value of the second reflecting property is different from the value of the first reflecting property. For example, the second signal 120 is reflected by variable reflector 106 that has been adjusted to have the second reflecting property. A second reflected signal 126 is produced from the portion of the second signal 120 being reflected. The second reflected signal 126 continues to propagate through the sample material 118.

Between the time the portion of the first signal 120 is reflected and the portion of the second signal 120 is reflected, the reflecting property of the reflector is modified from the first reflecting property to the second reflecting property. For example, the reflecting property can be modified by manually replacing a first reflector having the first reflector property with a second reflector having a second reflector property. According to exemplary embodiments where the variable reflector 106 is used to reflect the first signal 120 and second signal 120, the variable reflector 106 is controlled, for example by controller 108, to be adjusted from the first reflecting property to the second reflecting property prior to reflecting the portion of the second signal 120.

According to various exemplary embodiments where the transmitting of signals from the transmitter 102 is synchronized with the adjusting of the reflecting property of the variable reflector 106, the variable reflector 106 is controlled to be adjusted to the first reflecting property before the transmitter 102 transmits the first signal 120. After reflecting the portion of the first signal 120, the variable reflector is controlled to be adjusted to the second reflecting property. After the variable reflector 106 is adjusted to the second reflecting property, the transmitter 102 transmits the second signal 120 at step 920. For example, synchronization of the transmitter 102 with the variable reflector 106 is maintained through control provided by the controller 108.

At step 928, a second received signal is received. For example, the second received signal is received by the receiving element 114 of receiver 104. The second received signal includes the second reflected signal 126 that traveled through the sample material 118 and also an unreflected portion 128 of the second transmitted signal 120.

Referring back to FIGS. 2-5, a portion of the second signal 120 transmitted into the sample material 118 can be generally modeled as also having traveled over the path defined by vector A to reach the reflector 106. After being reflected by the reflector 106, the second reflected signal 126 that is produced can be generally modeled as also having traveled over the path denoted by the vector A' to reach the receiver 104. The second reflected signal 126 represents a portion of the second transmitted signal 120 that also traveled over the path 122 defined by vectors A and A'. The unreflected portion 128 of the second transmitted signal 120 can be generally modeled as also having traveled over the path denoted by the vector B to reach the receiver 104 without being reflected by the reflector 106. The first reflected signal 128 and the second reflected signal 128 provide an indication of at least one property of the sample material 118. By temporally spacing the first signal 120 and the second signal 120 apart from one another, the first reflected signal 128 and the second reflected signal 128 can be observed independently of one another.

Determining a Scalar-Type Property of the Material

Figure 7A:
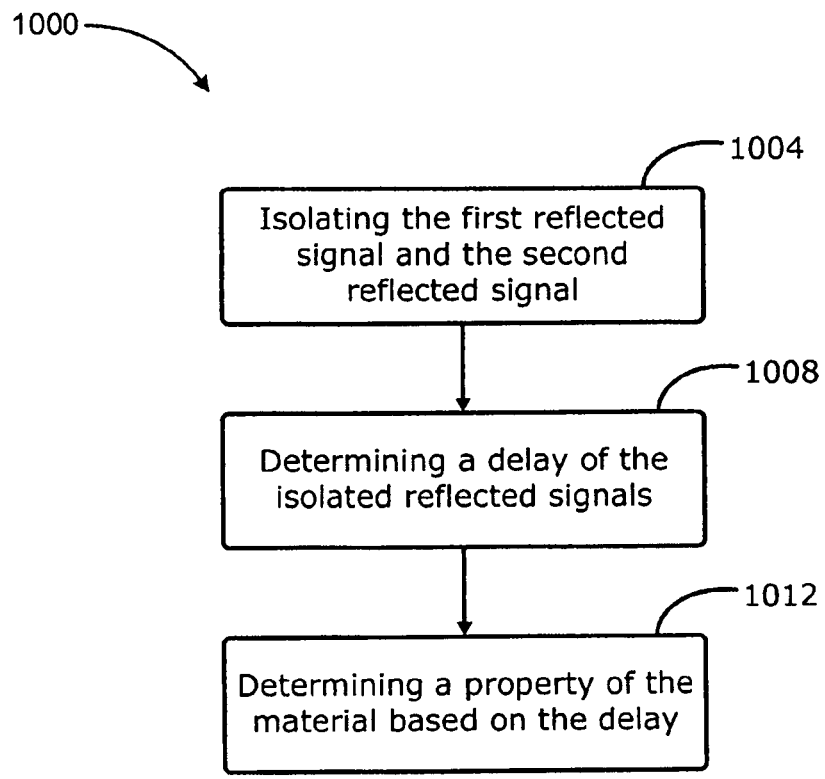
FIG. 7A is a schematic diagram of an exemplary method for determining at least one property of a sample material.

Referring now to FIG. 7A, therein illustrated is a schematic diagram of an exemplary method 1000 for determining at least one property of the sample material 118 based on the first received signal and the second received signal.

The first received signal can be expressed as:

$$o_i(t) = b_i(t) + a_i(t) + n_i(t)$$

where $b_i(t)$ is the unreflected portion 128 of the first transmitted signal 120, $a_i(t)$ is the first reflected signal 126, and $n_i(t)$ is random noise. For example, where the first received signal is rendered in discrete sampling data point format, $o_i(t)$ can be referred to as a trace or a time series of observation points.

Similarly, the second received signal can be expressed as:

$$o_k(t) = b_k(t) + a_k(t) + n_k(t)$$

where $b_k(t)$ is the unreflected portion 128 of the second transmitted signal 120, $a_k(t)$ is the second reflected signal 126, and $n_k(t)$ is random noise. For example, where the first received signal is rendered in discrete sampling data point format, $o_k(t)$ can be referred to a trace or a time series of observation points.

Referring back to FIG. 2, the signal path 122 traveled by the reflected signal 126 and generally defined by vectors A and A' can be modeled as having a path length $L_a$. Accordingly, there is a time delay $T_a$ between the time the transmitted signal 120 is transmitted from the transmitter 102 and the time the reflected signal 126 is received at the receiver 104. Since the first reflected signal 126 and the second reflected signal 126 both represent portions of transmitted signals that propagated over the signal path 122 defined by vectors A and A', and that both signals have the same velocity $v_a$ when traveling through the sample material 118, the time delay between the transmitting of a signal from the transmitter 102 and the receiving of the reflected signal 126 can be represented as:

$$T_a = \frac{L_a}{v_a}$$

The unreflected signal 128 travels over a signal path defined by vector B can be modeled as having a path length $L_b$. Accordingly, there is a time delay $T_b$ between the time the transmitted signal 120 is transmitted from the transmitter 102 and the time the unreflected signal 128 is received at the receiver 104. Since the unreflected first signal 128 and unreflected second signal 128 both represent portions of the transmitted signals that propagated over the signal path 123 defined by vector B, and have the same velocity $v_b$, the time delay between the transmitting of a signal from the transmitter 102 and the receiving of the unreflected signal 128 can be represented as:

$$T_b = \frac{L_b}{v_b}$$

According to various exemplary embodiments where the first transmitted signal 120 and the second transmitted signal 120 have substantially the same characteristics and is a transient signal, both signals can be represented by a wavelet w(t). Assuming that the wavelet signal w(t) is not substantially distorted over either reflected signal path 122 or unreflected signal path 123, an observation of the first received signal can be represented as:

$$o_i(t) = b\ w(t-T_b) + M_i w(t-+n_i(t)$$

where b represents the amplitude of signal coupling over the unreflected path 123, $bw(t-T_b)$ represents the unreflected first signal 128, $M_i$ represents the value of the amplitude of signal coupling over the reflected signal path 122 combined with the first reflecting property at which the portion of the first transmitted signal 120 is reflected, and $M_i\ w(t-T_a)$ represents the first reflected signal 126.

It will be understood that term of "amplitude of signal coupling" as used herein represents the factor of a change in the amplitude of a portion of a received signal (for example a portion representing the unreflected signal or a second portion representing the reflected signal) in relation to the transmitted signal. For example, the amplitude of signal coupling can depend on the properties of the system, such as properties of a container used to hold the sample material. The amplitude of signal coupling can also depend on properties of the material, including material absorption or attenuation.

An observation of the second received signal can be represented as:

$$o_k(t) = b\ w(t-T_b) + M_k w(t-+n_k(t)$$

where b represents the attenuation over the unreflected path B, $b\ w(t-T_h)$ represents the unreflected second signal 128, $M_j$ represents the value of the amplitude of signal coupling over the reflected signal path combined with the second reflecting property at which the portion of the second transmitted signal 120 is reflected, and $M_k\ w(t-T_a)$ represents the second reflected signal 126.

Observation $o_i(t)$ corresponds to an observation made by the receiver 104 between the time first reflected signal 120 is transmitted and the time the receiving of the first reflected signal 126 is completed. Observation $o_k(t)$ corresponds to an observation made by the receiver 104 between the time second reflected signal 120 is transmitted and the time the receiving of the second reflected signal 126 is completed. For example, the transmitter 102 and the receiver 104 can be synchronized such that a receiver 104 begins an observation when transmitter 102 transmits a signal into the sample material 106. It will be appreciated that while the transmission of the first signal 120 and the transmission of the second signal 120 can be spaced apart temporally, $M_i\ w(t-T_a)$ and $M_k\ w(t-T_a)$ representing the first reflected signal 126 and second reflected signal 126 respectively both have the same time delay $T_a$ in observations $o_i(t)$ and $o_k(t)$.

At step 1004, the first reflected signal 126 and the second reflected signal 126 are isolated. For example, the reflected signals can be isolated by calculating a difference between the observation $o_i(t)$ of the first received signal 126 and the observation $o_k(t)$ of the second received signal 126. For example, the difference can be calculated by the signal processor in the measurement system 100 or by the external signal processor. The result of the difference can be represented as:

$$o_i(t) - o_k(t) = (M_i - M_k) w(t-T_a) + n_i(t) - n_k(t)$$

It will be appreciated that because the first transmitted signal 120 and the second transmitted signal 120 have substantially the same characteristics, and that the unreflected first signal 128 and the second unreflected signal 128 both represent signals having traveled over the same path B, the unreflected portions 128 of the first signal 120 and the unreflected portion 128 of the second signal 120 are cancelled out from calculating a difference between the observation $o_i(t)$ of the first received signal and the observation $o_k(t)$ of second received signal. By contrast, due to reflecting the first signal 120 and the second signal 120 at different reflecting properties, calculating the difference between observation $o_i(t)$ and $o_k(t)$ leaves a non-zero portion $(M_i - M_k)w(t-T_a)$ representing the first reflected signal 126 and second reflected signal 126. For example, where the first reflecting property is a first reflectivity and the second reflecting property is a second reflectivity different from the first reflectivity, the resulting non-zero portion is similar to the transmitted first signal 120 or second signal 120, but having a different amplitude. Accordingly, the first reflected signal 126 and the second reflected signal 126 are isolated.

According to various exemplary, where the amplitude of the isolated first reflected signal and second reflected signal 126 is sufficiently high, the noise portions $n_i(t) - n_k(t)$ of the first received signal and the second received signal can be negligible with respect to the first reflected signal 126 and second reflected signal 126. Accordingly, the noise portions can be omitted.

Alternatively, where the noise is random and zero mean in character, steps 904 to 928 of method 900 can be repeated a plurality of times, each time using a consistent first reflecting property at step 912 and a consistent second reflecting property at step 924. Furthermore, the difference between the first received signal and the second received signal can be calculated for each repetition of steps 904-928. The plurality of the calculated differences can be averaged to further isolate the first reflected signal 126 and the second reflected signal 126. For example, the noise portion of the averaged calculated difference can be represented as:

$$\langle n_j(t) - n_k(t) \rangle = 0$$

where the $\langle a \rangle$ expression denotes an expected or average value (ex:

$$\langle a \rangle = \frac{\sum_i a_i}{N}$$

where i=1 to N)

For example, the isolated first and second reflected signals can be represented as:

$$\langle o_j(t) - o_k(t) \rangle = (M_j - M_k)w(t - T_a)$$

At step 1008, the time delay, of the isolated first and second reflected signals is determined. The delay can be determined according to an event picking or identification process that defines where a characteristic of the excitation signal occurs in time. This delay represents the time required by a transmitted signal 120 transmitted from the transmitter 102 traveling over the reflected path 122 defined by vectors AA' to reach the receiver 104 as a received signal 130. For example, this delay is represented by $T_a$. Where the transmitted signal 120 is a compact pulse of a short oscillatory signal, or similar excitation waveform, determination or estimation of delay $T_a$ can be carried out according to known methods commonly used in analysis of seismic data, ultrasonic data or similar data.

At step 1012, a property of the material is determined based on the delay. For example, the electrical permittivity of the material affects the velocity at which a signal travels through the material. Preferably, the first and second reflecting properties are different reflectivity when carrying out step 1012 to determine the electrical permittivity of the sample material. However, other types of reflecting properties can also be used. Referring back to FIGS. 2 to 5, if the length of the reflected signal path 122 is known, the velocity $v_a$ of a signal can be calculated according to:

$$v_a = \frac{L_a}{T_a}$$

If the measurement apparatus measures electromagnetic wave properties, then it is common practice to estimate the dielectric permittivity, K, of the material using the relationship:

$$K = \left(\frac{c}{v_a}\right)^2 = \left(\frac{cT_a}{L_a}\right)^2$$

where c is the speed of light in vacuum. For example, the calculations of the velocity and permittivity can be carried out by the signal processor in the measurement system 100 or external to the measurement system 100.

According to an alternative exemplary embodiment, the first transmitted signal 120 and second transmitted signals 120 are periodic signals. The first transmitted signal 120 and second transmitted signal 120 have substantially the same characteristics. For example, the periodic transmitted signal can be represented by:

$$w(t) = e^{j\omega t}$$

where $j = \sqrt{-1}$.

Assuming that the w(t) is not substantially distorted over either path AA' or path B, the first received signal can be represented as:

$$o_j(t) = be^{j\omega t} + M_j e^{j\omega t} e^{-j\omega T_a} + n_j(t)$$

where b represents the attenuation over the unreflected path B, $be^{j\omega t}$ represents the unreflected first signal 128, $M_j e^{j\omega t} e^{-j\omega t_a}$ represents the first reflected signal 126, and $M_j$ represents the value of the first reflecting property at which the portion of the first transmitted signal 120 is reflected.

The second received signal can be represented as:

$$o_k(t) = be^{j\omega t} + M_k e^{j\omega t} e^{-j\omega T_b} + n_k(t)$$

where b represents amplitude of signal coupling over the reflected signal path path 123, $be^{j\omega t}$ represents the unreflected second signal 128, $M_k e^{j\omega t} e^{-j\omega T_a}$ represents the second reflected signal 128, and $M_k$ represents amplitude of signal coupling over the reflected signal path combined with the second reflecting property at which the portion of the second transmitted signal 120 is reflected.

At step 1004, the first reflected signal 126 and the second reflected signal 126 are isolated by also calculating a difference between the first and the second received signals. For example, the difference can be calculated by the signal processor in the measurement system 100 or the signal processor external to the measurement system 100. The result of the difference can be represented as:

$$O_j - O_k = e^{-j\omega T_a}(M_j - M_k) + n_j(t) - n_k(t)$$

It will be appreciated that because the first transmitted signal 120 and the second transmitted signal 120 have substantially the same characteristics, and that the unreflected first signal 128 and the second unreflected signal 128 both represent signals having traveled over the same unreflected signal path 123, the unreflected portion 128 of the first signal 120 and the unreflected portion 128 of the second signal 120 are canceled out from calculating a difference between the observation $o_j(t)$ of the first received signal and the observation $o_k(t)$ of second received signal. By contrast, reflecting the first signal 120 and the second signal 120 at different reflecting properties, calculating the difference between observation $o_j(t)$ and $o_k(t)$ leaves a non-zero portion representing the first reflected signal 126 and second reflected signal 126. For example, where the first reflecting property is a first reflectivity and the second reflecting property is a second reflectivity different from the first reflectivity, the resulting difference is similar to the transmitted first signal 120 or second signal 120, but having a different amplitude. Accordingly, the first reflected signal 126 and the second reflected signal 126 are isolated.

According to various exemplary, where the amplitude of the isolated first reflected signal 126 and the second reflected signal 126 is sufficiently high, the noise portions $n_j(t) - n_k(t)$ of the first received signal and the second received signal can be negligible with respect to the first reflected signal 126 and second reflected signal 126. Accordingly, the noise portions can be omitted.

Alternatively, where the noise is random and zero mean in character, steps 904 to 928 of method 900 can be repeated a plurality of times, each time using a consistent first reflecting property at step 912 and a consistent second reflecting property at step 924. Furthermore, the difference between the first received signal and the second received signal can be calculated for each repetition of steps 904-928. The plurality of calculated differences can be averaged to further isolate the first reflected signal and the second reflected signal. For example, the noise portion of the averaged calculated difference can be represented as:

$$\langle n_j(t) - n_k(t) \rangle = 0$$

where the <a> expression denotes an expected or average value.

For example, the isolated first reflected signal 126 and second reflected signal 126 can be represented as:

$$\langle O_j - O_k \rangle = e^{-i\omega T_a}(M_j - M_k)$$

At step 1008, a phase delay of the isolated first and second reflected signals is determined. This phase delay represents the time required by transmitted signal 120 transmitted from the transmitter 102 traveling over the path AA' to reach the receiver 104 as a reflected signal 126. For example, this delay is represented by $\varphi_a = \omega T_a$. The phase delay can be determined using techniques known in the art, such as waveform digitization, Fourier transform, phase locked measurements, signal mixing.

At step 1012, a property of the material is determined based on the delay. For example, the electrical permittivity of the material affects the velocity at which a signal travels through the material. Preferably, the first and second reflecting properties are different reflectivities when carrying out step 1012 to determine the electrical permittivity of the sample material. However, other types of reflecting properties can also be used. Referring back to FIGS. 5 to 8, if the length of the signal path 122 is known, the velocity of a signal can be calculated according to:

$$v_a = \frac{L_a}{T_a} = \frac{L_a \omega}{\varphi_a}$$

If the measurement apparatus measures electromagnetic wave properties, then it is common practice to estimate the dielectric permittivity, K, of the material using the relationship:

$$K = \left(\frac{c}{v_a}\right)^2 = \left(\frac{cT_a}{L_a}\right)^2$$

where c is the speed of light in vacuum. For example, the calculations of the velocity and permittivity can be carried out by the signal processor the measurement system 100.

Figure 7B:
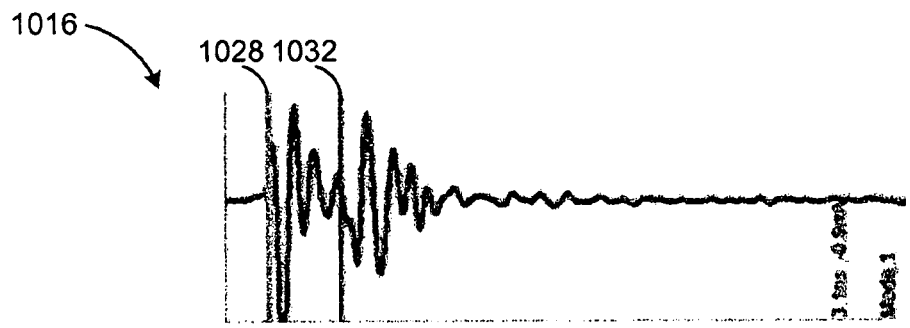
FIG. 7B illustrates an exemplary signal of a first received signal.
Figure 7C:
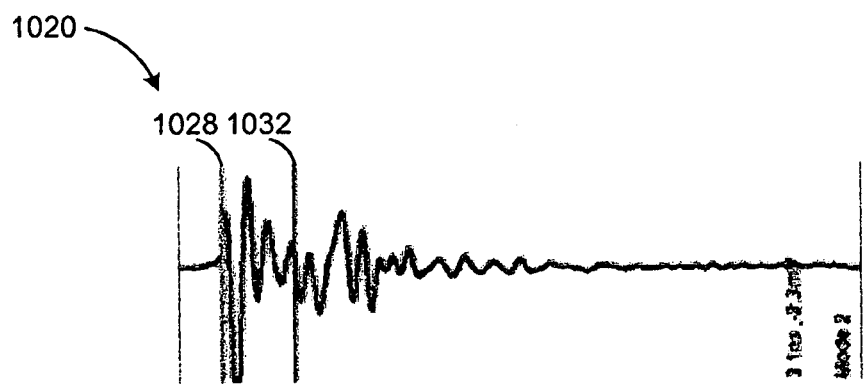
FIG. 7C illustrates an exemplary signal of a second received signal.
Figure 7D:
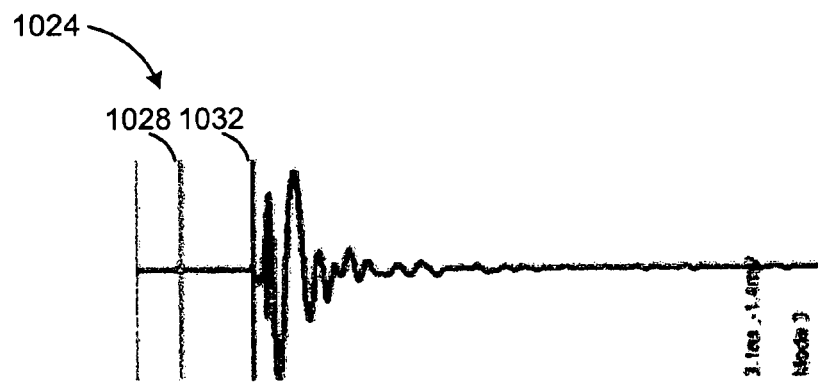
FIG. 7D illustrates a differential signal.

Referring now to FIGS. 7B to 7D, therein illustrated are exemplary signals of a first received signal 1016, a second received signal 1020 and a differential signal 1024 representing a difference between the first and second received signals, respectively. The first received signal 1016 and second received signal 1020 are illustrated to be aligned in time according to a signal start time 1028. A time delay 1032 represents the time required by transmitted signal 120 transmitted from the transmitter 102 traveling over the path AA' to reach the receiver 104 as a reflected signal 126 (as either first received signal 1016 or second received signal 1020). Between the signal start time 1028 and time delay 1032 only the unreflected portion 128 is received. It will be appreciated that this unreflected portion 128 is the same in the first received signal 1016 and the second 1020, such that taking a difference of the two signals results in differential signal 1024 having a substantially zero amplitude signal between its signal start time 1128 and the time delay 1032. Moreover, due to the first transmitted signal 120 and the second transmitted signal 120 being reflected at different reflecting properties at the reflector 106, the first received signal 1016 and the second received signal 1020 have different amplitudes. However, since both the first received signal 1016 and the second received signal 1020 include a same unreflected portion 120, this portion 120 is cancelled out in the differential signal 1024. The differential signal 1024 at times after the travel time delay resemble the transmitted signals 120, 120 (and also the unreflected portion 128 before the time delay), but has a different amplitude due to the first and second transmitted signals 120, 120 being reflected at different reflecting properties.

Determining a Orientation-Dependent Property of the Material

According to one exemplary embodiment, method 900 may be carried out to allow determination of anisotropy of a property of the sample material 118. Accordingly, steps of the method 900 are carried out a first time. During the first time, the first signal 120 is transmitted at step 904 and is subsequently reflected at step 908 such that the first received signal 130 is characterized by a first polarization of the signal. The received signal is sensitive to the specific transmitted signal polarization. Similarly, the second signal 120 is transmitted at step 920 and is subsequently reflected at step 924 such that the second received signal is also characterized by the first polarization of the signal. The first received signal 130 and the second received signal 130 provide an indication of the property of the sample material 118 for a first direction corresponding to the first polarization.

The steps of method 900 are then carried out a second time. During the second time, a third signal 120 is transmitted at step 904 and is subsequently reflected at step 908 such that the third received signal 130 is characterized by a second polarization of the signal that is different from the first polarization. For example, the second polarization is orthogonal to the first polarization. The received signal is sensitive to the specific transmitted signal polarization. Similarly, a fourth signal 120 is transmitted at step 920 and is subsequently reflected at step 924 such that the second received signal 130 is also characterized by the second polarization, which can be different and, in some cases, orthogonal to the first polarization. The third received signal and the fourth received signal then provide an indication of the property of the sample material 118 for a second orientation corresponding to the second polarization. The degree to which the property of the sample material 118 changes with different polarizations provides an indication of the anisotropy of a property of the sample material 118. Those skilled in the art will further understand that indications of anisotropy of a property of the sample material 118 in at least two directions can be used to determine anisotropy of the property over a range of direction. For example, indications of anisotropy of the property of the sample material 118 in the first direction and the second orthogonal direction can be used to fully characterize the anisotropy of the material of the sample material 118. Indications of anisotropy of the property of the sample material 118 in different directions can be further used to determine that the sample material isotropic.

According to one exemplary embodiment, the transmitting element 110 is adjustable to emit signals at different polarizations. For example, the transmitting element 110 can be a dual transmitting element capable of selectively transmitting signals at the first polarization or the second polarization. In some cases, the first polarization and the second polarization are orthogonal to each other. Alternatively, transmitting element 110 includes a rotatable element, wherein rotation of the element provides adjustment of the polarization of the signals 120 emitted from the transmitting element 110. For example, the element 110 can be attached to a rotatable mount.

Similarly, the receiving element 114 is also adjustable to receive signals at different polarizations. For example, the receiving element 114 can be a dual receiving element capable of selectively receiving signals at the first polarization or the second polarization. In some cases, the first polarization and the second polarization are orthogonal to each other. Alternatively, the receiving element 114 includes a rotatable element, wherein rotation of the element provides adjustment of polarization of the signals that can be received by the receiving element 114. For example, the receiving element 114 can be attached to a rotatable mount.

Where transmitting element 110 and receiving element 114 are adjustable and selectable in polarization, the variable reflector 106 is not required to have a field directional reflectivity dependence although the reflector 106 must have an adjustable reflectivity to modulate the amplitude of the reflected signals.

Referring back to FIG. 6, when carrying out the method 900 according to various exemplary embodiments using adjustable transmitting element 110 and adjustable receiving element 114 to determine anisotropy of a property of the sample material, at step 904, the first signal 120 is transmitted at the first polarization.

At step 908, the portion of the first signal 120 travelling through the sample material 118 is reflected at a first reflecting property. For example, the first signal 120 is reflected by the variable reflector 106 that has been adjusted to a first reflectivity. Due to the reflecting, the amplitude of the first reflected signal 126 can be different from the first signal 120, while the polarization of the first reflected signal 126 is maintained in relation to the first signal 120.

At step 912, the first received signal is received. For example, the first received signal 1300 is received by the receiving element 114 of receiver 104. The first received signal includes the first reflected signal 126 that traveled through the sample material 118 with the defined first polarization and also an unreflected portion 128 of the first transmitted signal 120.

At step 920, the second signal 120 is transmitted at the first polarization, which is the same polarization as the first signal 120.

At step 924, the portion of the second signal 120 travelling through the sample material 118 is reflected at a second reflecting property. For example, the second signal 120 is reflected by the variable reflector 106 that has been adjusted to a second reflectivity different from the first reflectivity. For example, the variable reflector 106 is adjusted to the second reflectivity after reflecting the first signal 120 and prior to reflecting the second signal 120. Due to the reflecting, the amplitude of the second reflected signal 126 can be different from the second signal 120. The amplitude of the second reflected signal 126 is also different from the amplitude of the first reflected signal 126, while the polarization of the second reflected signal 126 is the same as the polarization of the first reflected signal 126.

At step 928, the second received signal is received. For example, the second received signal is received by the receiving element 114 of receiver 104. The second received signal includes the second reflected signal 126 that traveled through the sample material 118 with the defined polarization and also an unreflected portion 128 of the second transmitted signal 120.

The first received signal 130 and the second received signal 130 can be used to determine a physical property for a first direction corresponding to the first defined polarization of the exciting waveform signals 120 and 120.

Continuing with FIG. 6, the method 900 can be carried out a second time, wherein a third signal and fourth signal are transmitted at steps 904 and 920 respectively at a second polarization. The second polarization is different from the first polarization at which the first and second signals were transmitted. For example, the second polarization is orthogonal to the first polarization. At step 904, a third signal 120 is transmitted at the second polarization.

At step 908 of the second time of carrying out method 900, the portion of the third signal 120 travelling through the sample material 118 is reflected at a first reflecting property. For example, the third signal 120 is reflected by the variable reflector 106 that has been adjusted to a first reflectivity. Due to the reflecting, the amplitude of the third reflected signal 126 can be different from the third signal 120, while the polarization of the third reflected signal 126 is maintained in relation to the third signal 120.

At step 912, the third received signal with the different field polarization is received. For example, the third received signal is received by the receiving element 114 of receiver 104. The third received signal includes the third reflected signal 126 that traveled through the sample material 118 with the defined polarization and also an unreflected portion 128 of the third transmitted signal 120.

At step 920, the fourth signal 120 is transmitted at the second polarization, which is the same polarization as the third signal 120.

At step 924, the portion of the fourth signal 120 travelling through the sample material 118 is reflected at a second reflecting property. For example, the fourth signal 120 is reflected by the variable reflector 106 that has been adjusted to a second reflectivity different from the first reflectivity reflecting the third signal. For example, the variable reflector 106 is adjusted to the second reflectivity after reflecting the third signal 120 and prior to reflecting the fourth signal 120. Due to the reflecting, the amplitude of the fourth reflected signal 126 can be different from the fourth signal 120. The amplitude of the fourth reflected signal 126 is also different from the amplitude of the third reflected signal 126, while the polarization of the fourth reflected signal 126 is the same as the polarization of the third reflected signal 126.

At step 928, the fourth received signal is received. For example, the fourth received signal is received by the receiving element 114 of receiver 104. The fourth received signal includes the first reflected signal 126 that traveled through the sample material 118 with the defined second polarization and also an unreflected portion 128 of the third transmitted signal 120. The third received signal 130 and the fourth received signal 130 can be used to determine a physical property for a second direction corresponding to the second defined polarization of the third and fourth exciting waveform signals 120 and 120.

It will be understood that the first polarization signals can be processed in a manner similar to the scalar property determination described herein to characterize by a first element of a tensor material property and the second differing polarization signals can be processed to characterize by a second element of a tensor material property. This is in contrast to determination of sample material 118 properties that are direction-independent, wherein the received signals can be characterized by a scalar, and characterization of a signal direction is not necessary.

Anisotropic properties of the sample material 118 can be determined based on direction-dependent properties. For example, properties of the sample material 118 in a first direction corresponding to the first polarization of the signal 120 can be determined from analysis of the first and second received signals for the first polarization. Similarly, properties of the sample material 118 in a second polarization direction corresponding to the polarization can be determined from analysis of the third and fourth received signals with the differing second polarization.

According to another exemplary embodiment, the variable reflector 106 has adjustable directional reflectivity and can be adjusted to reflect signals in a selected range of polarizations. The variable reflector 106 can be adjusted to reflect in one instance signals having a first polarization and in another instance signals having a second polarization. For example, the first polarization is orthogonal to the second polarization. For example, the variable reflector 106 can be a reflector 106 having differently oriented and independently controllable reflecting elements. Alternatively, the variable reflector 106 can be reflector 106 having a rotatable reflecting face.

Where the variable reflector 106 is field direction dependent and can be adjusted to reflected signals in a selected range of polarizations, the transmitting element 110 can be field direction independent. The transmitting element 110 can emit signals in a large range of polarizations. For example, the transmitting element 110 can emit a signal having mixed polarization meaning that the emitted signal always contains field components that are not aligned with the variable reflector directional character.

Referring back to FIG. 6, when carrying out the method 900 according to various exemplary embodiments using an adjustable direction dependent variable reflector 106, at step 904 the first signal 120 is transmitted with a mixed polarization.

At step 908, the portion of the first signal 120 travelling through the sample material 118 is reflected at the variable reflector 106 such that only the portion of the first signal 120 having a polarization aligned with the first direction of the variable reflector is reflected with a first reflectivity. For example, the variable reflector 106 can modulate the reflectivity of the portion of the first signal having its polarization aligned with the variable reflector direction.

At step 912, the first received signal is received. For example, the first received signal is received by the receiving element 114 of receiver 104. The first received signal includes the first reflected signal 126 that traveled through the sample material 118 and also an unreflected portion 128 of the first transmitted signal 120.

At step 920, the second signal 120 is transmitted with the same mixed polarization as the first signal.

At step 924, the portion of the second signal 120 travelling through the sample material 118 is reflected at the variable reflector 106 such that only the portion of the second signal 120 having a polarization aligned with the first direction of the variable reflector is reflected with a second reflectivity. The variable reflector 106 can further modulate the reflectivity of the portion of the second signal 120.

At step 928, the second received signal is received. For example, the second received signal is received by the receiving element 114 of receiver 104. The second received signal includes the second reflected signal 126 that traveled through the sample material 118 and also an unreflected portion 128 of the second transmitted signal 120.

Continuing with FIG. 6, the method 900 can be carried out a second time, wherein a third signal and a fourth signal are transmitted and the variable reflector 106 is adjusted such that it only reflects signals having a second polarization. The second polarization is different from the first polarization, and in some cases can be orthogonal to the first polarization.

At step 904 a third signal 120 is transmitted with a mixed polarization.

At step 908, the portion of the third signal 120 travelling through the sample material 118 is reflected at the variable reflector 106 such that only the portion of the third signal 120 having a polarization aligned with the second direction of the variable reflector is reflected with a first reflectivity. For example, the variable reflector 106 can modulate the reflectivity of the portion of the third signal having its polarization aligned with the variable reflector direction.

At step 912, the third received signal is received. For example, the third received signal is received by the receiving element 114 of receiver 104. The third received signal includes the first reflected signal 126 that traveled through the sample material 118 and also an unreflected portion 128 of the third transmitted signal 120.

At step 920, the fourth signal 120 is transmitted with the same mixed polarization as the third signal.

At step 924, the portion of the second signal 120 travelling through the sample material 118 is reflected at the variable reflector 106 such that only the portion of the fourth signal 120 having a polarization aligned with the second direction of the variable reflector is reflected with a second reflectivity. For example, the variable reflector 106 can further modulate the reflectivity of the portion of the fourth signal 120.

At step 928, the fourth received signal is received. For example, the fourth received signal is received by the receiving element 114 of receiver 104. The fourth received signal includes the fourth reflected signal 126 that traveled through the sample material 118 and also an unreflected portion 128 of the fourth transmitted signal 120.

It will be understood that the first reflector direction signals can be processed in a manner similar to the scalar property determination to characterize by a first element of a tensor material property and the second reflector direction signals can be processed to characterize by a second element of a tensor material property. This is in contrast to determination of sample material 118 properties that are direction-independent, wherein the received signals can be characterized by a scalar, and characterization of a signal direction is not necessary.

Anisotropic properties of the sample material 118 can be determined based on direction-dependent reflector properties For example, properties of the sample material 118 in a first direction corresponding to the polarization of the signal 120 aligned with the first reflector direction can be determined from analysis of the first and second received signals for the first reflector direction. Similarly, properties of the sample material 118 in a second polarization direction corresponding to the polarization of the signal 120 aligned with the second reflector direction can be determined from analysis of the third and fourth received signals for the second reflector direction.

Those skilled in the art of vector and tensor analysis will recognize that a number of variations on these base cases can be developed that accomplish the measurement objective.

Determining a Frequency-Dependent Property of the Material

According to one exemplary embodiment, method 900 may be carried out to allow determination of a frequency dependent property of the sample material 118. The first signal 120 is transmitted at step 904 and is subsequently reflected at step 908 such that the first received signal has analyzable frequency characteristics. Similarly, the second signal 120 is transmitted at step 920 and is subsequently reflected at step 924 such that the second received signal also has analyzable frequency characteristics.

According to one exemplary embodiment, the signal generator 112 of the transmitter 100 can emit an excitation signal having a non-zero amplitude over a wide range of frequencies. For example, an excitation signal 120 emitted from the transmitter 100 has substantially the same amplitude over a determined frequency range. Importantly, the frequency response of the emitted excitation signal 120 is known. For example, the emitted excitation signal can be formed by simultaneously emitting a plurality of sinusoidal signals, a swept chirp over a range of frequencies, transmission of a wideband, and other known methods of sending a wideband signal.

The variable reflector 106 can be frequency dependent and can be adjusted in order to have a test reflectivity in a test frequency range corresponding to a first frequency range. The test reflectivity in the test frequency range is differentiable from the reflectivity of the variable reflector 106 at frequencies outside the test frequency range. For example, the test reflectivity in the test frequency range can be increased and decreased while the reflectivity at frequencies outside the test frequency range remains fixed. By having different reflectivities in different frequency ranges, it is possible to analyze frequency dependent properties of the sample material 118. For example, where the test reflectivity in the test frequency range is greater than the reflectivity of the reflector 106 at frequencies outside the test frequency range, it is possible to analyze the properties of the sample material 118 in that test frequency range corresponding to the first frequency range.

The variable reflector 106 can be further adjusted to adjust boundaries of the test frequency range. For example the variable reflector 106 can be adjusted so that the test frequency range corresponds to a second frequency range that is different from the first frequency range. For example the second frequency range can slightly overlap with the first frequency. Adjusting the boundaries of the test range allows the analysis of the frequency dependent properties of the sample material 118 on a different range of frequencies.

Referring back to FIG. 6, when carrying out the method 900 according to various exemplary embodiments using an adjustable frequency dependent variable reflector 106, at step 904 a first signal 120 having a non-zero amplitude over a wide of range of frequencies is transmitted.

At step 908, the portion of the first signal 120 travelling through the sample material 118 is reflected at the variable reflector 106. The variable reflector 106 is adjusted so that it has the test reflectivity in the test frequency range corresponding to a first frequency range. At least a portion of the first frequency range is a sub-range of the range of frequencies where the first signal 120 has non-zero amplitude. As a result, the first reflected signal 126 has distinguishable characteristics in the frequency range corresponding to the first frequency range. For example, where the test reflectivity in the test frequency range is greater than the reflectivity in frequency ranges outside the test frequency range and the first signal 120 has a substantially constant amplitude over its own sub-range, the first reflected signal 126 should have a greater amplitude in the frequency range corresponding to the first frequency range. It will be appreciated that reflecting the first signal 120 at the test reflectivity in the test frequency range corresponding to the first frequency range has the effect of isolating signals limited to the first frequency range.

At step 912, the first received signal is received. For example, the first received signal 130 is received by the receiving element 114 of receiver 104. The first received signal 130 includes the first reflected signal 126 that traveled through the sample material 118 and also an unreflected portion 128 of the first transmitted signal 120.

At step 920, a second signal 120 having a nonzero amplitude over a wide range of frequencies is transmitted. For example, the second signal is substantially the same as the first signal 120, namely that the second signal 120 also has a non-zero amplitude in the same wide range of frequencies of the first signal 120.

At step 924, the portion of the second signal 120 travelling through the sample material 118 is reflected at the variable reflector 106. For example, before reflecting the second signal 120, the variable reflector 106 is adjusted so that it has the test reflectivity in its test frequency range corresponding to a second frequency range that is different from the first frequency range. At least a portion of the second frequency range is a sub-range of the range of frequencies where the second signal 120 has non-zero amplitude. As a result, the second reflected signal 126 has distinguishable characteristics in the frequency range corresponding to the second frequency range. For example, where the test reflectivity in the test frequency range is greater than the reflectivity in frequency ranges outside the test frequency range and the second signal 120 has a substantially constant amplitude over its own sub-range, the second reflected signal 126 should have a greater amplitude in the frequency range corresponding to the second frequency range. It will be appreciated that reflecting the second signal 120 at the test reflectivity in the test frequency range corresponding to the second frequency range has the effect of isolating signals limited to the second frequency range.

At step 928, the second received signal is received. For example, the second received signal is received by the receiving element 114 of receiver 104. The second received signal includes the second reflected signal 126 that traveled through the sample material 118 and also an unreflected portion 128 of the second transmitted signal 120.

Since first reflected signal 126 has distinguishable characteristics in the first frequency range, the first received signal can be analyzed to determine properties of the sample material 118 limited to the first frequency range. Similarly, since the second reflected signal 126 has distinguishable characteristics in the second frequency range, the second received signal can be analyzed to determined properties of the sample material 118 limited to the second frequency range.

Steps 904 to 912 of method 900 can be repeated, wherein the variable reflector 106 is adjusted so that the test frequency range corresponds to different ranges of frequencies. This allows for determination of properties of the sample material 118 over multiple ranges of frequencies.

According to one exemplary embodiment, differently spatially located reflecting surfaces 124 are used for reflecting transmitted signals 120. The variable reflector 106 can have a plurality of reflecting surfaces 124 that can be simultaneously mounted onto a surface of the sample material 118. When mounted on the surface of the sample material 118, each reflecting surface 124 of the variable reflector covers a different location of the surface of the sample material. Additionally, the transmitter 102 can have more than one transmitting element 110 and the receiver 104 can have more than one receiving element 114. For example, the plurality of transmitting element 110 can be simultaneously mounted onto the surface of the sample material 118 and can be positioned at different locations of the surface of the sample material. For example, the plurality of receiving element 114 can be simultaneously mounted onto the surface of the sample material 118 and can be positioned at different locations of the surface of the sample material. The plurality of differently spatially located reflecting surfaces 124 can be used to examine the spatial variation of at least one property of the sample material 118.

According to various exemplary embodiments, method 900 for measuring a property of a sample material 118 can be repeated over a duration of time. Where the sample material 118 is a fluid or loose solid, the method 900 and 1000 can be repeated in order to monitor the variability of the sample material 118 as a function of time.

According to various exemplary embodiments, method 900 for measuring a property of a sample material 118 can be repeated over an extended duration of time. For example, a sample material 118, including some static materials, can have time-varying properties. For example, soils being wetted or drained (rain fall followed by dry weather) and curing of concrete have time-varying properties. Accordingly methods 900 and 1000 can be repeated over the extended duration of time in order to monitor the variation of the property as a function of time.

Figure 8:
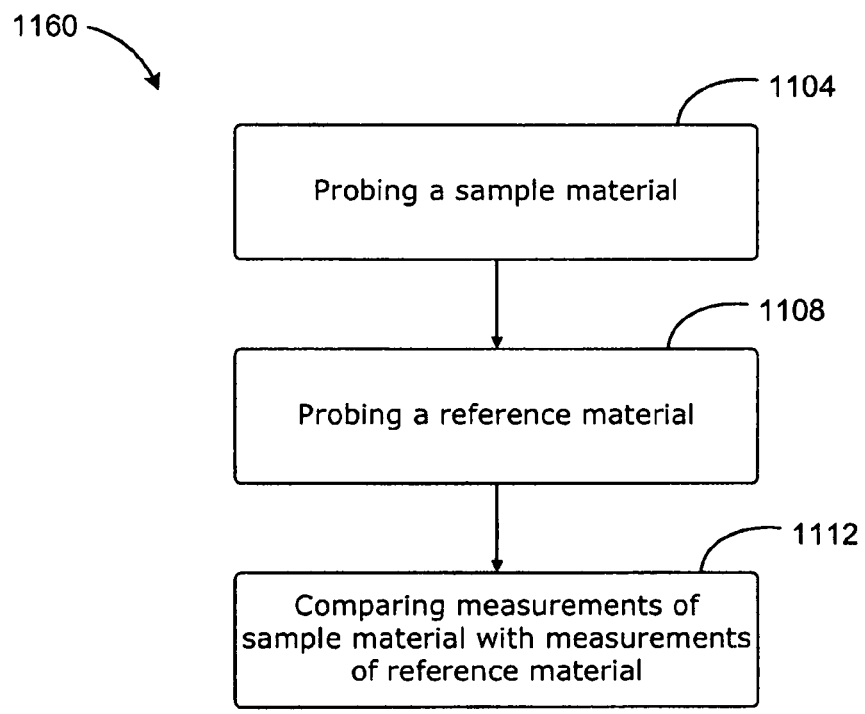
FIG. 8 is a schematic diagram of an exemplary method for determining a property of a sample material

Referring now to FIG. 8, therein illustrated is a schematic diagram of a method 1100 for determining a property of a sample material 118 based on known properties of a reference material.

At step 1104, the sample material is provided. The sample material 118 is further probed according to the method 900. A first signal 120 and a second signal 120 are transmitted at steps 904 and 908. A portion of the first signal 120 is reflected at a first reflecting property at step 912. A portion of the second signal 120 is reflected at a second reflecting property at step 920. A first received signal that includes the first reflected signal 126 and a second received signal that includes the second reflected signal 126 are received at step 924 and step 928 respectively.

At step 1108, the reference material is provided. The reference material has known properties. Furthermore, some of the dimensions of the reference material should be substantially the same as the dimensions of the sample material 118. The signal path traveled by a signal between the transmitter 102, variable reflector 106 and receiver 104 through the reference material should be equivalent to the signal path 122 traveled by a signal through the sample material 118. The reference material is further probed according to the method 900. For example, a third signal is transmitted into the reference material at step 904 and fourth signal is transmitted into the reference material at step 908. The third signal is reflected at a third reflecting property at step 912. The third reflecting property can be the same as, or different from, the first reflecting property. The fourth signal is reflected at fourth reflecting property at step 920. The fourth reflecting property can be the same as, or different from, the second reflecting property. A third received signal that includes the third reflected signal and a fourth received signal that includes the fourth reflected signal are received at step 924 and step 928 respectively.

At step 1112, the first received signal and the second received signal received from probing the sample material 118 are compared with the third received signal and the fourth received signal received from probing the reference material. The comparison is carried out in order to determine a property of the sample material based on at least one known property of the reference material. For example, the correlation can be carried out by the signal processor of the measurement system 100.

According to various exemplary embodiments, the comparison of step 1112 can be carried out in order to determine a velocity of the transmitted signal through the sample material 118. The comparison of step 1112 can be carried out in order to also determine an attenuation factor of the sample material.

As previously described herein, a difference between the first received signal and a second received signal can be calculated in order to isolate the first reflected signal 126 and the second reflected signal 126 that traveled through the sample material 118. A plurality of first signals and second signals can be transmitted through the sample material 118 and the calculated difference can be averaged. The difference of the first received signal and the second received signal can be represented as:

$$\langle o_j^1 - o_k^1 \rangle = (M_j^1 - M_k^1)w(t - T_a^1)$$

Similarly a difference of the third received signal and the fourth received signal can be calculated in order to isolate the third reflected signal and the fourth reflected signal that traveled through the reference material. A plurality of third signals and fourth signals can be transmitted through the reference material and the calculated difference can be averaged. The difference of the third received signal and the fourth received signal can be represented as:

$$\langle o_j^R - o_k^R \rangle = (M_j^R - M_k^R)w(t - T_a^R)$$

Where a velocity $v_R$ of the signal through the reference material can be known based on known properties of the reference material, the velocity $v_a$ of the sample material can be determined based on the travel time $T_a^1$ of a signal over the reflected signal path 122 through sample material 118 and the travel time $T_a^R$ of a signal over an equivalent path through the reference material. For example, the velocity $v_a$ can be determined according to the equation:

$$v_a = v_R \frac{T_a^R}{T_a^1}$$

The sample material 118 and the reference material can have different attenuation factors along the reflected signal path 122. The factor of change in amplitude of a signal traveling through the sample material 118 over the reflected signal path 122 can be represented as $e^{-\alpha_1 L_a}$ where $\alpha_1$ is the attenuation of the sample material 118 and $L_a$ is the length of the signal path 122. Similarly the factor of change in amplitude of a signal traveling through the reference material over the reflected signal path 122 can be represented as $e^{-\alpha_R L_a}$ where $\alpha_R$ is the attenuation of the reference material and $L_a$ is the length of the signal path 122. It will be appreciated that attenuation can be represented as occurring exponentially due to energy dissipation in material and that the amplitude will fall off as a function of path length.

The ratio of the difference between the first received signal and the second received signal with the difference between the third received signal and the fourth can be represented as:

$$\frac{(M_j^1 - M_k^1)}{(M_j^R - M_k^R)} = C \frac{e^{-\alpha_1 L_a}}{e^{-\alpha_R L_a}}$$

The C factor reflects the fact that the material change may change the intrinsic element coupling of energy to and from the material. With proper design, C~1 can be achieved. For example purposes, C is herein understood as equaling 1. The observed signal will depend on the material attenuation and changes in modulated reflector response.

Taking the natural logarithm of numerator and the denominator of the equation:

$$\frac{(M_j^1 - M_k^1)}{(M_j^R - M_k^R)} = \frac{e^{-\alpha_1 L_a}}{e^{-\alpha_R L_a}}$$

provides the relationship:

$$\frac{\ln(M_j^1 - M_k^1)}{\ln(M_j^R - M_k^R)} = \frac{\alpha_1}{\alpha_R}$$

attenuation $\alpha_1$ of the sample material 118 can then be written in terms of the reference sample attenuation and the amplitude of the modulation ratio:

$$\alpha_1 = \alpha_R \frac{\ln(M_j^1 - M_k^1)}{\ln(M_j^R - M_k^R)}$$

Figure 9:
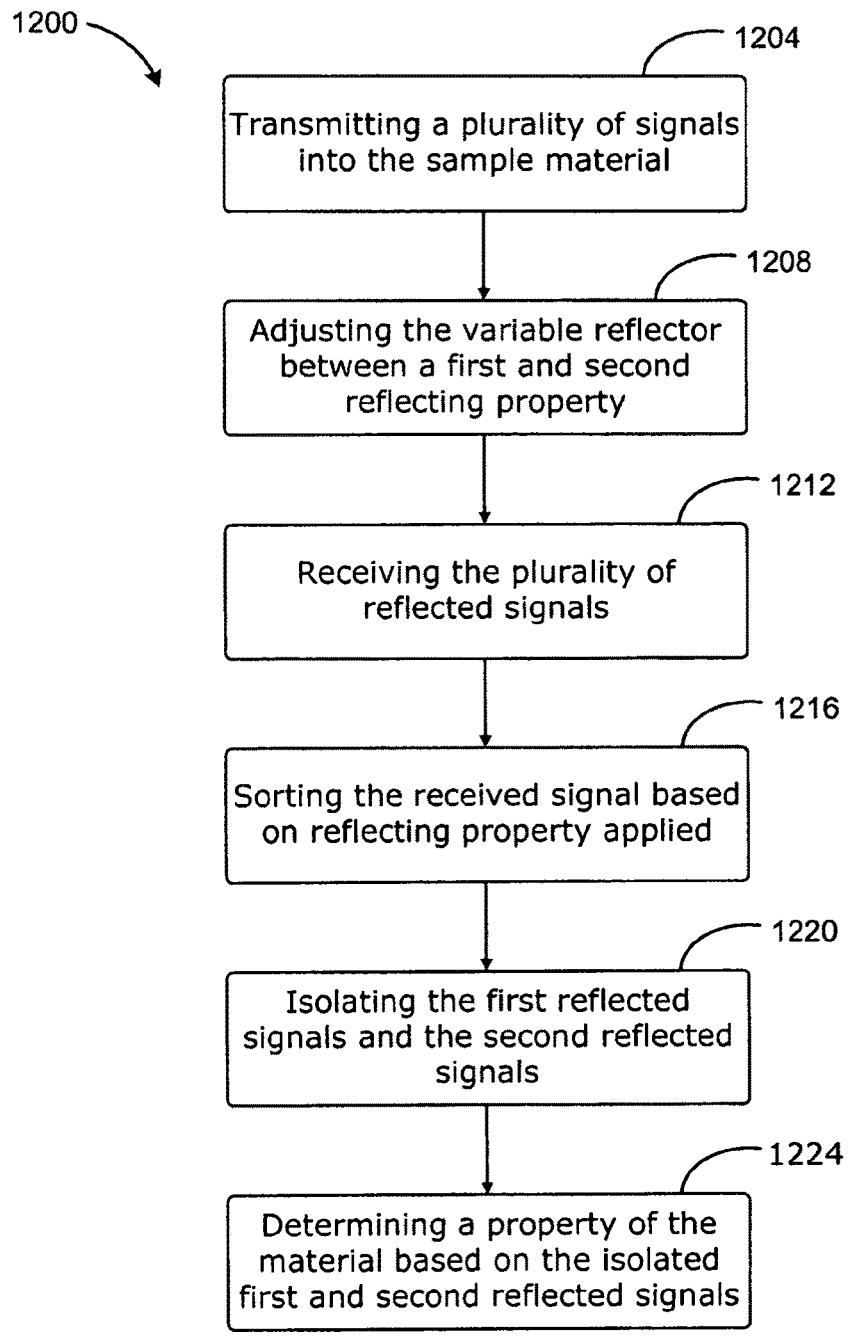
FIG. 9 is a schematic diagram of an exemplary unsynchronized method for determining a property of a sample material.

Referring now to FIG. 9, therein illustrated is a schematic diagram of an unsynchronized method 1200 for determining a property of a sample material 118 according to various exemplary embodiments. Advantageously, the method 1200 does not require synchronization between the time of sending a signal 120 from the transmitter 102 and the time of adjusting a reflecting property of the variable reflector 106.

At step 1204, a plurality of signals 120 is transmitted into the sample material 118. The signals 120 are transmitted sequentially in time and over a duration that is substantially longer than the amount of time taken to adjust the reflecting property of the variable reflector 106.

At step 1208, during the duration of time in which the plurality of signals 120 is being transmitted from the transmitter 102, the reflecting property of the variable reflector 106 is adjusted at least once. The variable reflector 106 is adjusted at least from a first reflecting property to a second reflecting property. According to some exemplary embodiments, the variable reflector 106 can be further adjusted from the second reflecting property back to the first reflecting property. The adjusting of the reflecting property of the variable reflector 106 while the transmitting of the signals 120 is ongoing has the effect that a first subset of the plurality of signals are reflected at the first reflecting property and a second subset of the plurality of the transmitted signals 120 are reflected at the second reflecting property.

At step 1212, a plurality of the reflected signals 126 are received at the receiver 104. The reflected signals 126 include signals reflected at the first reflecting property and signals reflected at the second reflecting property.

For example, step 1204 and step 1212 can form a loop, wherein in each cycle of the loop a signal 120 is transmitted at step 1204, and the corresponding reflected signal 126 is received at the receiver 102 at step 1212. For example, two adjacent transmissions of signals 120 at step 1204 of two cycles of the loop can be sufficiently spaced apart in time such that the unreflected portion 128 of the later transmitted signal does not interfere with the reflected portion 126 of the earlier transmitted signal. The time between the beginning of a transmission of signal 120 at step 1204 and a completion of the reception of the corresponding received signal at step 1212 defines one observation $o_j(t)$ made by the receiver 102. It will be appreciated that one observation is made per cycle of the loop of steps 1204 and 1212. As a result, a plurality of observations $o_j(t)$ are made.

Step 1208 is carried out during the repeating of the loop formed by step 1204 and 1212, but the timing of adjusting the variable reflector 106 at step 1208 is not synchronized with any individual transmission of the signal 120 at step 1204 or any individual reception of the received signal at step 1208. Accordingly, the variable reflector 106 can be understood as being asynchronous with the transmitter 102 and receiver 104.

At step 1216, the plurality of received signals are sorted based on whether an individual signal 120 was reflected at the first reflecting property or at the second reflecting property. For example, where the received signals are received by the receiver 104 as a plurality of observations $o_j(t)$, an average $o_a(t)$ of the observations is calculated:

$$o_a(t) = \frac{1}{N} \sum_{j=1}^{N} o_j(t)$$

For an individual observation $o_j(t)$ corresponding to one of the received signals, a difference $o_j'(t)$ is calculated according to:

$$o_j'(t) = o_j(t) - o_a(t)$$

Since only the portion of the received corresponding to the reflected signal 126 and noise is present in the difference $o_j'(t)$, the difference can be expressed as:

$$o_j'(t) = \pm \frac{(M_2 - M_1)}{2} w(t - T_a) + n_j(t)$$

wherein the ± signs reflects the fact that the difference can correspond to either a signal 120 reflected at the first reflecting property or the second reflecting property. Assuming $n_j(t)$ is small, then a received signal can be sorted based on the individually determined differences $o_j'(t)$ into two groups depending on the sign of the dominant event.

$$g_j^+(t) = o_j'(t) \text{ if sign positive } j=1, N_+$$

wherein $g_j^+(t)$ corresponds to signals reflected at the first reflecting property, $$g_j^-(t) = o_j'(t) \text{ if sign negative } j=1, N_-$$

wherein $g_j^-(t)$ corresponds to signals reflected at the second reflecting property and $g_j^?(t) = o_j'(t)$ if sign indeterminate $j=1,N_?$ wherein $g_j^?(t)$ corresponds to signals that does not allow a clear determination of how the signal 120 was reflected. An average of the sorted signals determined as being reflected at the first reflecting property is computed according to:

$$\langle g^+(t) \rangle = \frac{1}{N_+} \sum_{j=1}^{N_+} g_j^+(t)$$

An average of the stored signals determined as being reflected at the second reflecting property is computed according to:

$$\langle g^-(t) \rangle = \frac{1}{N_-} \sum_{j=1}^{N_-} g_j^-(t)$$

A difference of the average of the signals reflected at the first reflecting property and the average of the signals reflected at the second reflecting property can be computed according to:

$$\langle g^+(t) \rangle - \langle g^-(t) \rangle = (M_2 - M_1) w(t - T_a)$$

It will be appreciated that this equation is similar to the isolated first and second reflected signals calculated at steps 1004 of method 1000. Various properties of the sample material 118 can then be determined according to methods described herein. For example, an electrical permittivity of the sample material 118 can be determined based on the time delay $T_a$ and a path length $L_a$.

The steps of method 1200 for determining a property of the material can be performed as part of step 1104 of probing a sample material 118 of method 1100. The steps of method 1200 can also be performed as part of step 1108 of probing a reference material of method 1100. The first and second received signals determined at step 1104 of probing the sample material 118 and the isolated third and fourth received signals determined from step 1108 of probing the reference material can then be correlated at step 1112 in order to determine one or more properties of the sample material 118. For example, a permittivity of the sample material 118 and/or an attenuation factor of the sample material 118 can be calculated.

While various exemplary embodiments have been described with reference to reflecting transmitted signals 120 at a first reflecting property and a second reflecting property, it will be understood that transmitted signals 120 can be further reflected at additional reflecting properties. Signals received from being reflected at the additional reflecting properties can be further used to determine one or more properties of the sample material 118. Exemplary methods described herein can be further adapted for the reflecting of transmitted signals 120 at additional reflecting properties.

According to various exemplary embodiments, at least one transmitter 102, at least one receiver 104, and at least one variable reflector 106 can be provided as a kit As described elsewhere herein, the transmitter 102 can transmit a plurality of signals into a material to be measured, the variable reflector can reflect signals propagating through the material to be measured at at least a first reflecting property and a second reflecting property, and the receiver can receive a plurality of signals propagating through the material to be measured. For example, the transmitter 102, receiver 104 and variable reflector 106 can be transported separately, and assembled on-site to form the measurement system 100 described herein. For example, the kit 1300 can further include the controller 108 for controlling the transmitter 102 and the receiver 104, and optionally the variable reflector 106. Alternatively, one or more of the transmitter 102, receiver 104, and variable reflector 106 can connect with an external controller, such as a computer device or handheld device in order to receive various control signals. For example, the kit 1300 can further include a non-transitory computer-readable medium upon which a plurality of instructions are stored for carrying out various exemplary methods described herein. The plurality of instructions include at least instructions for controlling the at least one transmitter 102 to transmit the first signal; controlling the at least one transmitter 102 to transmit the second signal; controlling the at least one variable reflector 106 to adjust the reflecting property of the reflected between the first reflecting property and the second reflecting property; and isolating the first received signal and the second received signal.

Figure 10:
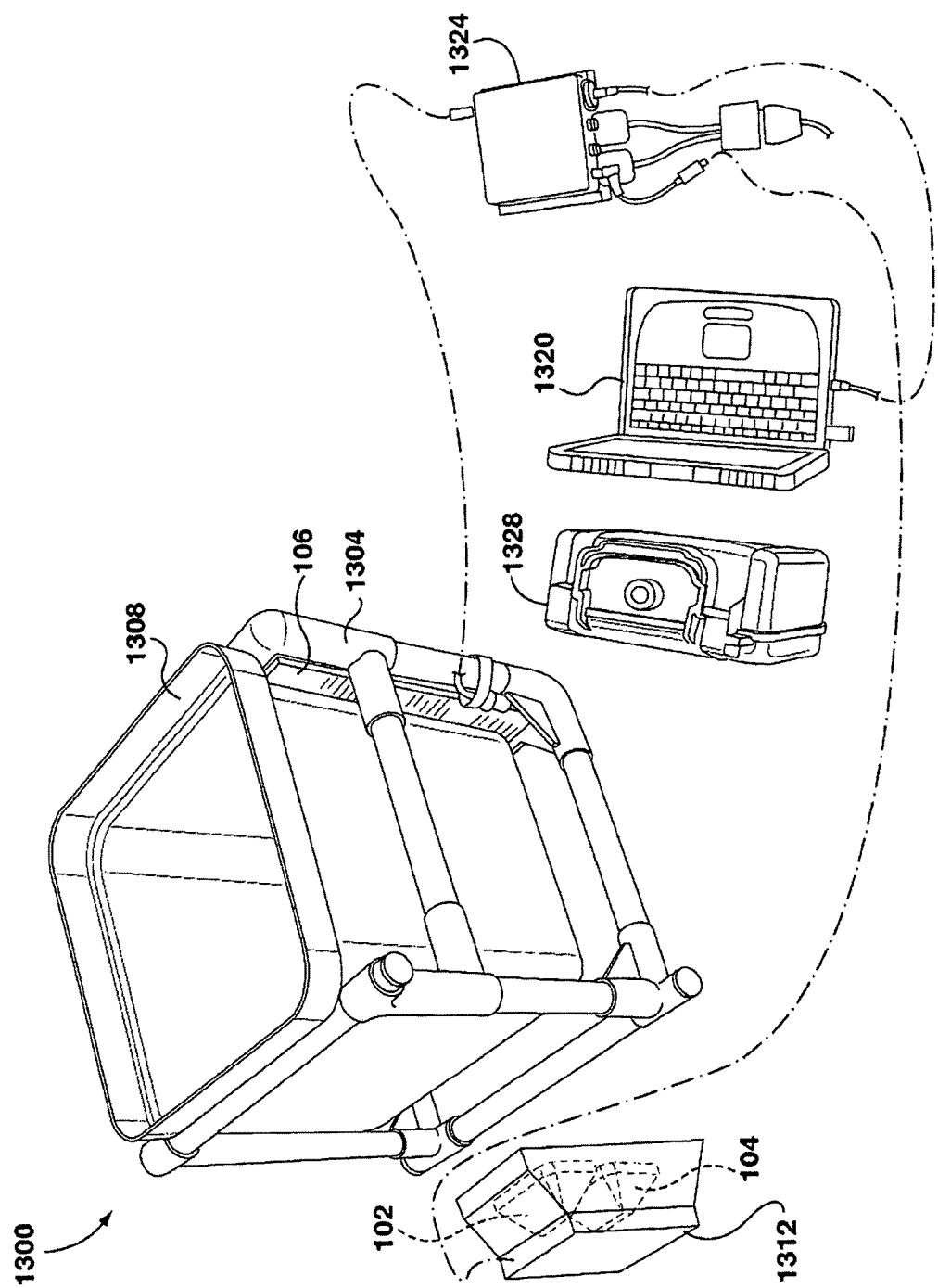
FIG. 10 is a perspective view of a kit for determining a property of a sample material.

Referring now to FIG. 10, therein illustrated a perspective view of an exemplary packaged measurement system 1300 that is ready for field use. The packaged measurement system 1300 includes a support frame 1304 for supporting a sample material 118 to be measured. The packaged measurement system 1300 may further include a container 1308 for holding the sample material 118 (ex: where the sample material 118 is a fluid or has a plurality of discrete pieces). The container 1308 is formed of a material that is permeable to electromagnetic signals and which has known properties. The support member 1304 provides for mounting thereto a transmitter 102 and a receiver 104 such that signals transmitted from the transmitter 102 and received at the receiver 104 substantially only travel through the sample material 118 supported by the support frame 1304. The support member 1304 further provides mounting thereto a reflector 106 at a position opposite the mounted transmitter 102 and receiver 104. In this way, signals transmitted from the transmitter 102 travel through the sample material 118 being supported and is reflected by the reflector 106. Signals reflected by the reflector 106 further travel through the sample material 118 to be received at the receiver 104.

According to the example illustrated in FIG. 10, the transmitter 103 and receiver 104 are packaged within a single transducer unit 1312. For example, the single transducer unit 1312 can be a transducer unit used in ground penetrating radar (GPR) applications. For example, the single transducer unit can be the TR1000™ transducer provided by Sensor and Software.

An input/output port 1316 of the transducer unit 1312 may be further connected to an input/output device 1320, which may be laptop, tablet, smartphone, or other suitable devices known in the art. For example, the transducer 1312 communicates with the input/output device 1320 via an interface device 1324. For example the interface device 1324 may be a SPIDAR™ network interface controller provided by Sensor and Software.

The transducer unit 1312 may provide functions of the controller 108 as described herein. Alternatively, the input/output device 1320 may provide functions of the controller 108. Alternatively, functions provided by controller 108 of the measurement system may be share and/or split amount the transducer unit 1312 and the input/output device 1320.

The packaged measurement system 1300 may further include a power supply 1328. The power supply 1328 may be a portable battery for portable deployment of the packaged measurement system 1320.

According to some exemplary embodiments where the mounted reflector 106 is a controllable variable reflector, the input/output device 1320 may be further connected to the variable reflector 106 to selectively change reflecting properties of the variable reflector 106.

Figure 11:
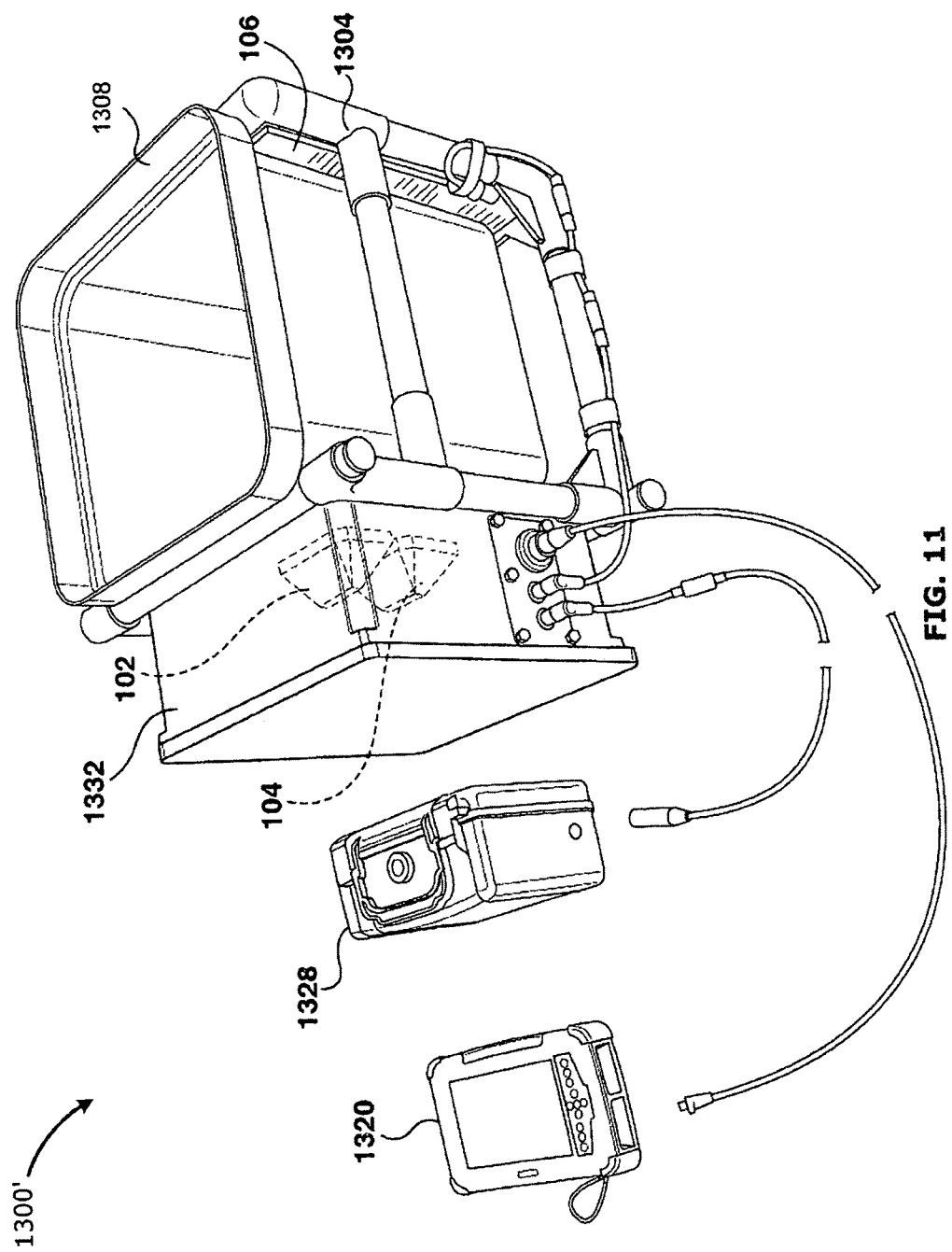
FIG. 11 is a perspective view of a kit for determining a property of a sample material.

Referring now to FIG. 11, therein illustrated is a perspective view of an alternative exemplary packaged measurement system 1300' that is ready for field use. The alternative packaged measurement system 1300' is provided with the transmitter 102 and receiver 104 enclosed within an enclosure 1332 already mounted onto the support frame 1304 opposite the reflector 106. The interface device 1324 providing communication between the input/output device 1320 and the variable reflector 106 may also be enclosed within the enclosure 1332. Accordingly the enclosure 1332 presents a first input/output port for connection to the input/output device, a second port for connection with a power supply and, where applicable, a third port for connection with a variable reflector 106 for selectively adjusting reflecting properties thereof.

Figure 12:
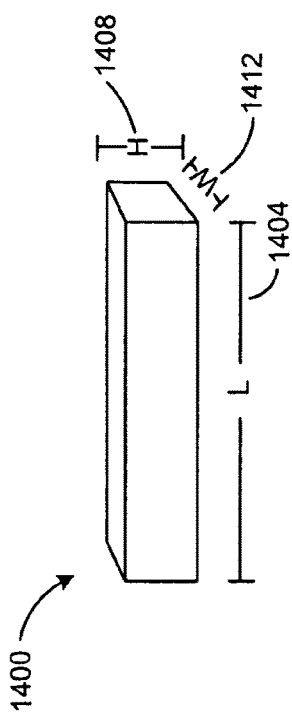
FIG. 12 illustrates a perspective view of one conductive element according to various exemplary embodiments.

Referring now to FIG. 12, therein illustrated is an exemplary elongated conductive element 1400. The elongated conductive element 1400 can be energized by an incident electromagnetic field. "Energizing a conductive element" or variations thereof herein refers to the conductive element receiving energy from the electromagnetic field and having a flow of current through it as a result of receiving that energy.

The elongated conductive element 1400 provided in various exemplary embodiments is selected to have a length 1404 that is substantially less than characterizing features of incident electromagnetic signals that are expected to energize the elongated conductive element 1400. In particular, the length 1404 of the elongated conductive element 1400 is shorter than a pulse duration or a wavelength of expected incident electromagnetic signals. The elongated conductive element further has a shape wherein its length 1404 is substantially greater than its cross-sectional dimension (width 1408 and height 1412). Due to the elongated shape of the conductive element 1400, an incident electromagnetic signal causes a current to flow in the direction of the lengths of the conductive element 1400 while the current in other directions are negligible. Furthermore, due to the elongated shape of the conductive element 1400, the conductive element 1400 is substantially energized by the directional component of the incident electromagnetic signal that is substantially parallel to the orientation of the length of the conductive element 1400. Components of the incident electromagnetic signal in other directions do not have a significant energizing effect on the conductive element 1400.

When there is electrical current flow through the conductive element 1400, the conductive element 1400 creates a scattered electromagnetic field in the space surrounding the conductive element 1400. The amount of scattering can be represented by the following expressions described in [1]:

TABLE 5-1

Fields of a Short Electric Dipole

| Component | General Expression | Far Field | Quasi-Stationary |
|---|---|---|---|
| $E_r$ | $\dfrac{[I]L\cos\theta}{2\pi\varepsilon_0}\left(\dfrac{1}{cr^2}+\dfrac{1}{j\omega r^3}\right)$ | 0 | $\dfrac{q_0\,L\cos\theta}{2\pi\varepsilon_0 r^3}$ |
| $E_\theta$ | $\dfrac{[I]L\sin\theta}{4\pi\varepsilon_0}\left(\dfrac{j\omega}{c^2 r}+\dfrac{1}{cr^2}+\dfrac{1}{j\omega r^3}\right)$ | $\dfrac{[I]Lj\omega\sin\theta}{4\pi\varepsilon_0 c^2 r}=\dfrac{j60\pi[I]\sin\theta}{r}\dfrac{L}{\lambda}$ | $\dfrac{q_0\,L\sin\theta}{4\pi\varepsilon_0 r^3}$ |
| $H_\varphi$ | $\dfrac{[I]L\sin\theta}{4\pi}\left(\dfrac{j\omega}{cr}+\dfrac{1}{r^2}\right)$ | $\dfrac{[I]Lj\omega\sin\theta}{4\pi cr}=\dfrac{j[I]\sin\theta}{2r}\dfrac{L}{\lambda}$ | $\dfrac{I_0\,L\sin\theta}{4\pi r^2}$ |

The restriction applies that $r \gg L$ and $\lambda \gg L$. The quantities in the table are in SI units, that is, E in volts per meter, H in amperes per meter, I in amperes, r in meter, etc. Three of the field components of an electric dipole are everywhere zero, that is,
$E_\varphi = H_r = H_\theta = 0$ wherein I is the current amplitude through the conductive element 1400, L is the length 104 of the current element, r, θ, φ are spherical polar coordinates with r being the distance of the observation point from the center of the conductive element 1400 and θ the angle between the axis of the conductive element 1400 and the radial direction to the observation point, c is the speed of light vacuum, ω is a frequency of the scattered electromagnetic signal.

As a result of an incident electromagnetic signal impinging on the electrical conductive element 1400 and energizing the conductive element 1400, a scattered electromagnetic field is created by the conductive element 1400. Where there are no other sources energizing the conductive element 1400, the scattered electromagnetic field is caused only by the incident electromagnetic signal energizing the conductive element 1400. Accordingly, properties of the scattered electromagnetic field will depend only on properties of the incident electromagnetic signal, properties of the conductive element 1400 and properties of the space surrounding the conductive element 1400. Where properties of the conductive element 1400 and surrounding space are known, it is possible to determine characteristics of an incident electromagnetic signal based on measurement of the scattered signal. Similarly, where properties of conductive element 1400 and the incident signal are known, it is possible to determine characteristics of the surrounding space based on measurement of the scattered electromagnetic signal.

The energizing and scattering performed by conductive element 1400 can be understood as reflecting received incident electromagnetic signal to produce a scattered (reflected) electromagnetic signal. The relationship between the incident electromagnetic signal and the reflected scattered electromagnetic field can be understood as a reflecting property of the conductive element 1400.

According to various exemplary embodiments, the conductive element can be formed of a metallic wire section or of metalized deposits on a dielectric (insulating) substrate.

Figure 13:
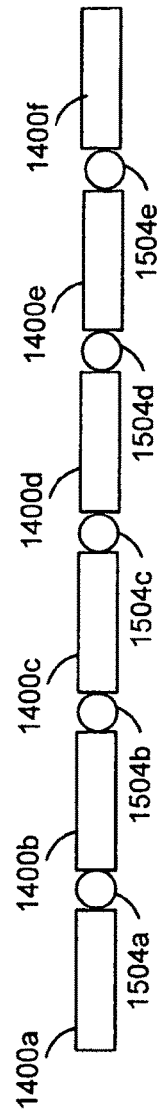
FIG. 13 illustrates a plan view of an exemplary interconnection of conductive elements.

Referring now to FIG. 13, therein illustrated is a plan view of an exemplary interconnection 1500 of a plurality of conductive elements 1400 being interconnected by a plurality of variable impedance junction elements 1504. According to the example shown in FIG. 13, six conductive elements denoted as first conductive element 1400a, second conductive element 1400b, third conductive element 1400c, fourth conductive element 1400d, fifth conductive element 1400e and sixth conductive element 1400g are provided. According to the example shown in FIG. 13, five conductive elements denoted as first junction 1504a, second junction 1504b, third junction 1504c, fourth junction 1504d, and fifth junction 1504e are provided. The conductive elements 1400a-1400g are shown as being linearly arranged and positioned end to end. Each junction element 1504a-204f interconnects two adjacently positioned conductive elements 1400. While FIG. 13 illustrates an exemplary arrangement having six conductive elements 1400 and five junction elements 1504, it will be understood that any number of conductive elements 1400 and corresponding junction elements 1504 interconnecting the conductive elements 1400 may be used.

According to one exemplary embodiment, the junction elements 1504 are controllable to be varied between an insulating state and a conducting state. In the conducting state, a junction element 1504 provides a conducting electrical connection between the two conductive elements 1400 joined to the junction element 1504 to allow flow of electricity between the two conductive elements 1400. In the insulating state, the junction element 1504 electrically separates the two conductive elements 1400 joined to the junction element 208 such that electricity cannot flow between the two conductive elements 1400. For example, the junction elements 1504 can be diodes that can be toggled between an insulating state and a conducting state through application of a bias voltage. Alternatively, the junction elements 1504 can be photosensitive diodes that move between the insulating state and the conducting state depending on an amount of light incident upon the diodes.

Figure 14:
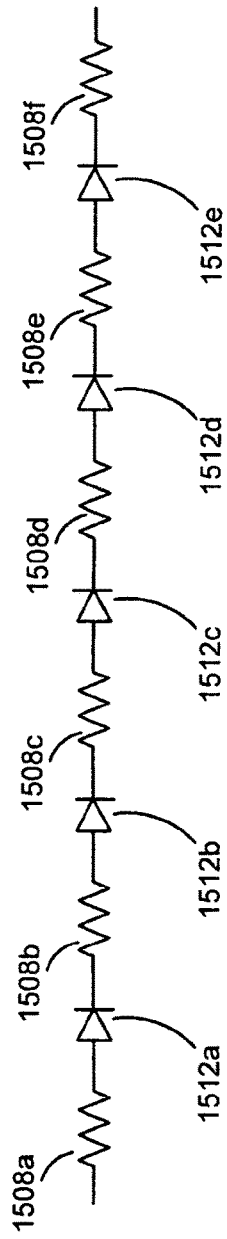
FIG. 14 illustrates a circuit diagram of the exemplary interconnection of FIG. 12.

Referring now to FIG. 14, therein illustrated is a schematic electrical circuit diagram of the connection of conductive elements 1400 and junction elements 1504. The conductive elements 1400a, 1400b, 1400c, 1400d, 1400e, 1400f can be represented by a plurality of electrical lines having respective line impedances 1508a, 1508b, 1508c, 1508d, 1508e, and 1508f. These lines are interconnected by diodes 1512a, 1512b, 1512c, 1512d, and 1512e which respectively represent the junction elements 1504a, 1504b, 1504c, 1504d, and 1504e. It will be understood that applying a positive bias voltage over a diode will cause conducting of electricity between two electrical lines 1508 connected to the diode. Conversely, applying a negative bias voltage at diode 1512 will cause two electrical lines 1508 connected to a diode 1512 to be electrically insulated. A diode 1512 is in the conducting state when a positive bias voltage is applied and it will be in the insulating state when a negative bias voltage is applied or no voltage is applied.

It will be appreciated that by providing electrical connection between the conductive elements 1400, the junction elements 1504 combine the conductive elements 1400 to form one or more combination conductive elements. The combination of conductive elements have lengths that are greater than the lengths 1404 of the individual conductive elements. For example, when each of the junction elements 1504a to 1504e of arrangement 1500 are in the conducting state, a combination conductive element is formed having a length equal to the combined lengths of the six conductive elements 1504a to 1504e.

Figure 15:
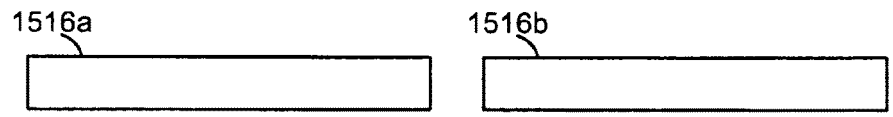
FIG. 15 illustrates a plan view of exemplary combination conductive elements formed from the interconnection of conductive elements of FIG. 12.

Further control of the junction elements 1504 allows the formation of different numbers of combination conductive elements having different lengths. For example, FIG. 15 illustrates two combination conductive elements 1516a and 1516b. First conductive elements 1516a is formed of first conductive element 1400a, second conductive element 1400b, and third conductive element 1400c being connected by junction elements 1504a and 1504b in the conducting state. Second conductive element 1516b is formed of fourth conductive element 1400d, fifth conductive element 1400e and sixth conductive element 1400f being connected by junction elements 1504d and 1504e in the conducting state. Third junction element 1504c is controlled to be in the insulating state to separate the first combination conductive element 1516a from the second combination conductive element 216b.

Figure 16:
FIG. 16 illustrates a plan view of exemplary combination conductive elements formed from the interconnection of conductive elements of FIG. 12.

For example, FIG. 16 illustrates another combination wherein three combination conductive elements 1516c, 1516d, and 1516e are formed. Third combination conductive element 1516c is formed of the first conductive element 1400a and second conductive element 1400b. Fourth combination conductive element 1516d is formed of the third conductive element 1400c and the fourth conductive element 1516d. Fifth conductive element 1516e is formed of the fifth conductive element 1400e and the sixth conductive element 1400f. First junction element 1504a, third junction element 1504c, and fifth junction element 1504e are controlled to be in the conducting state. Second junction element 1504b and fourth junction element 1504d are controlled to be in the insulating state.

It will be appreciated that control of the junction elements to vary the conducting state of different junction elements 1504 allows the variation of the effective lengths of the combination conductive elements from the conductive elements 1400. It will be further appreciated that the length of the combination conductive elements will be a multiple of the length of a single elongated conductive element 1400.

The strength of the current flow in a combination conductive element 1516 resulting from energizing by the incident electromagnetic signal will depend on the lengths of the combination conductive elements 1516 formed from the elongated conductive elements 1400. The strength of the scattered electromagnetic signal will also depend on the length of the combination conductive element 1516. Therefore, control of the variable impedance junction elements 1504 to vary the length of the combination conductive elements 216 that are formed provide a way for controlling the reflecting property of a reflector formed from the conductive elements 1400. As a result, varying the impedance of the variable impedance junction elements 1504 also varies the scattered electromagnetic signal scattered from the combination conductive elements. Varying the lengths of the combination conductive element 1516 varies frequency-related reflecting property of the reflector.

According to various exemplary embodiments, the junction elements 1504 are variable impedance elements that can be adjusted to have a desired impedance value within a range of possible impedances. For example, each junction element 1504 is a variable resistor. For example, the junction element 1504 is a diode or photo diode. According to some exemplary embodiments, the junction element 1504 is a resistive device that is sensitive to heat (thermal), sound (acoustic) or pressure. It will be understood that examples of junction elements 1504 provided herein are not intended to be exhaustive and other suitable elements having an adjustable impedance may be used for the junction element 1504. According to variable exemplary embodiments, the variable impedance junction elements 1504 can be controlled to be in an insulating state wherein flow of electricity between two conductive elements 1400 connected by the junction element 1504 is prevented. The variable impedance junction elements 1504 can be further controlled to be in a conducting state, wherein when in the conducting state the junction element 1504 can be further controlled to have a desired impedance value within the range of possible impedances.

According to some exemplary embodiments, the shift of the junction element 1504 between the conducting state and the insulating state occurs gradually through a continuous range of impedance values. Alternatively, the shift of the junction element 1504 between the conducting state and the insulating state occurs abruptly between the two states.

According to various exemplary embodiments, the impedance of the junction elements 1504 can vary based on environmental conditions. For example, various devices can be used that change electrical properties based on changing environmental conditions such as temperature, light, moisture, pressure. For example, the junction elements are thermistors.

Figure 17:
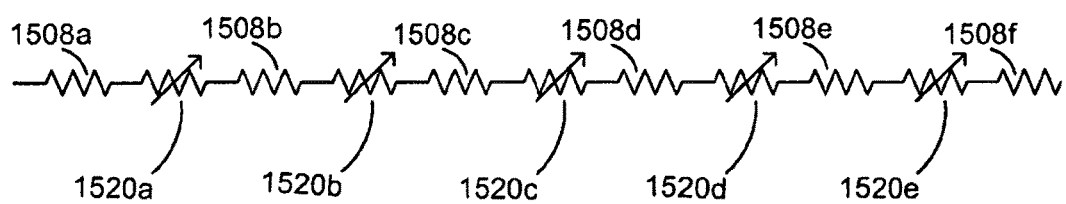
FIG. 17 illustrates a circuit diagram of the exemplary interconnection of FIG. 12.

Referring now to FIG. 17, therein illustrated is a schematic electrical circuit diagram of the connection of conductive elements 1400 and variable impedance junction elements 1504. The conductive elements 1400a, 1400b, 1400c, 1400d, 1400e, 1400f can be represented by a plurality of electrical lines having respective line impedances 1508a, 1508b, 1508c, 1508d, 1508e, and 1508f. These lines are interconnected by variable impedances 1520a, 1520b, 1520c, 1520d, and 1520e which respectively represent the variable impedance junction elements 1504a, 1504b, 1504c, 1504d, and 1504e. For example, the impedance of the junction elements 1504 can be adjusted by applying a DC bias to the ends the combination of conductive elements 1400. Alternatively, a DC bias can be applied to subsections of the combination of conductive elements 1400. When applying an electrical bias, care should be taken so that an electromagnetic response is not created in the conductive elements 1400. Alternatively, temperature change or light impinging or pressure or some other mechanism can also be used to control the impedance of the junction elements 1504.

Controlling of the junction elements 1504 allows for the combining of conductive elements 1400 to form one or more combination conductive elements. As described in relation to FIGS. 15 and 16, controlling the variable impedance conductive elements 1504 between conducting and insulating states allows the formation of combination conductive elements of variable lengths.

Figure 18:
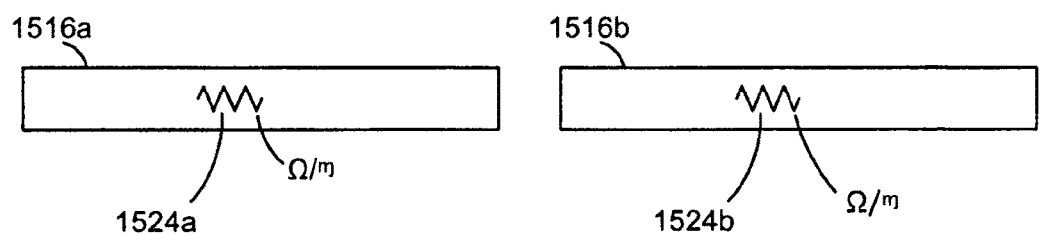
FIG. 18 illustrates a plan view of exemplary combination conductive elements from the interconnection conductive elements of FIG. 17.

Referring now to FIG. 18, therein illustrated are two combinations conductive elements 216a and 216. First combination conductive elements 216a is formed of first conductive element 1400a, second conductive element 1400b, and third conductive element 1400c being connected by junction elements 1504a and 204b in the conducting state. Second conductive element 216b is formed of fourth conductive element 1400d, fifth conductive element 1400e and sixth conductive element 1400f being connected by junction elements 1504d and 204e in the conducting state. Third junction element 1504c is controlled to be in the insulating state to separate the first combination conductive element 216a from the second combination conductive element 216b.

In addition to controlling the first junction element 1504a, second junction element 1504b, fourth junction element 1504d and fifth junction element 1504e to the conducting state, each of these junction element 1504 can be further controlled to a desired impedance value, which results in the varying of an effective impedance of the combination conductive elements formed from the conductive elements 1400. For example, effective impedance 1524a for the first combination conductive element 1516a is the sum of the impedance values of the first line impedance 1508a, first variable impedance 1520a, second line impedance 1508b, second variable impedance 1520b, and third line impedance 1508c. For example, effective impedance 1524b for the second combination conductive element 1516b is the sum of the impedance values of the fourth line impedance 1508d, fourth variable impedance 1520d, fifth line impedance 1508e, fifth variable impedance 1520e, and sixth line impedance 1508f. By varying both the length and the impedance of the combination conductive elements that are formed from the conductive elements 1400, effective impedance per unit lengths for the formed combination conductive elements can be achieved.

The strength of the current flow in a combination conductive element 1516 resulting from energizing by the incident electromagnetic signal will depend on the impedance of the combination conductive elements 1516 formed from the elongated conductive elements 1400. It will be appreciated that the scattered electromagnetic signal will also depend on the impedance of the combination conductive element 1516. Therefore, control of the variable impedance junction elements 1504 to vary the impedance per unit length of the combination conductive elements 1516 that are formed provides a way for controlling the reflecting property of a reflector formed from the conductive elements 1400. As a result, varying the impedance of the variable impedance junction elements 1504 also varies the scattered electromagnetic signal scattered from the combination conductive elements. In particular, the varying of the impedance per unit lengths of the combination conductive element 1516 varies the amplitude of the reflecting property of the reflector.

Figure 19:
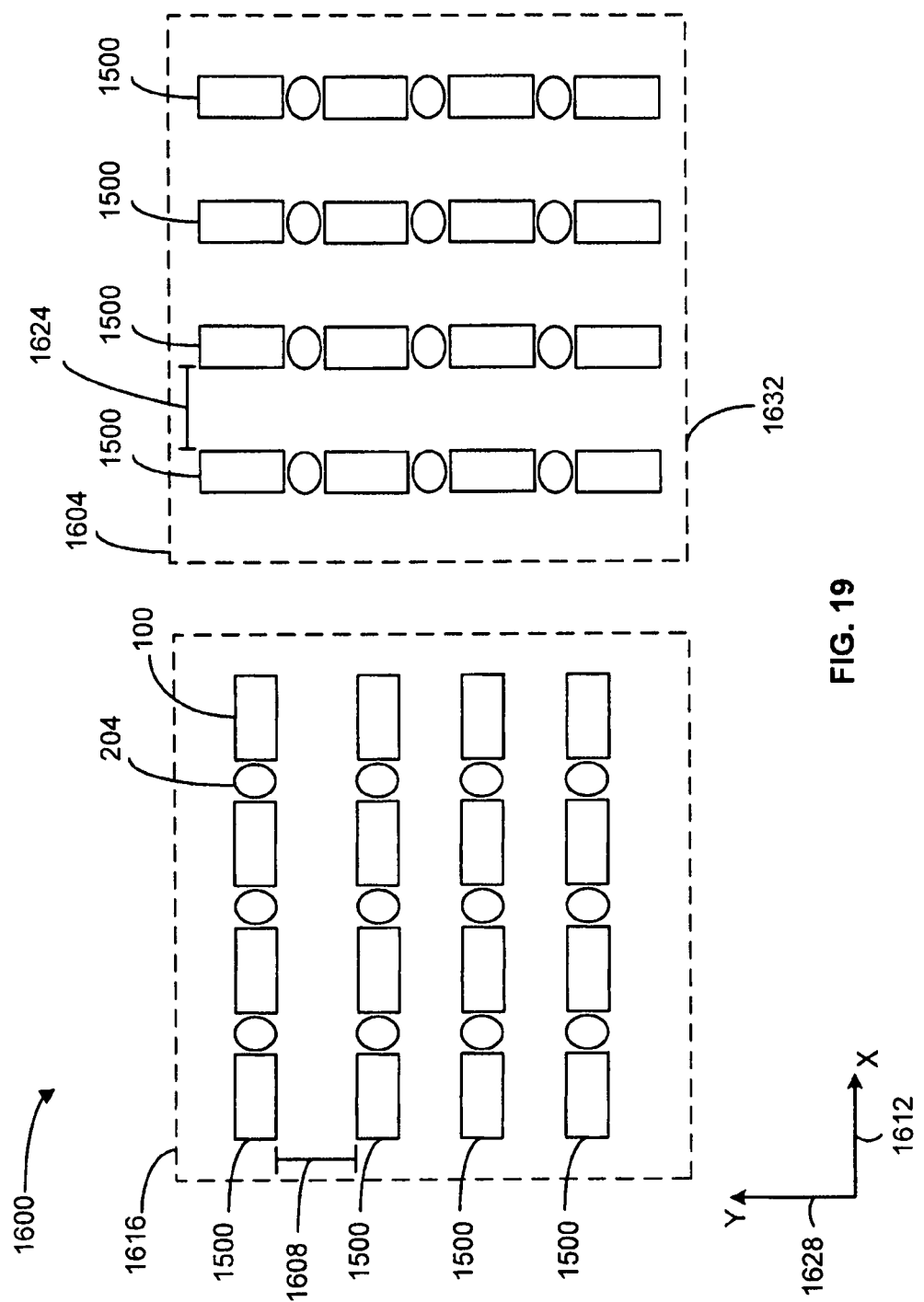
FIG. 19 illustrates a plan view of two variable reflectors according to various exemplary embodiments.

Referring now to FIG. 19, therein illustrated are plan views of a first exemplary planar variable reflector 1600 and a second exemplary planar variable reflector 1604 each having a plurality of interconnections 1500 of conductive elements 1400.

The first planar variable reflector 1600 includes a plurality of interconnections 200 that are placed side-by-side. The interconnections 1500 are spaced apart from one another by a distance 1608. For example, the distance 1608 of the spacing between the side-by-side interconnections 1500 is substantially greater than the width 1412 and height 108 of the conductive elements 1400 of the interconnections 1500. Accordingly, the strength of electromagnetic fields being reflected or scattered in a direction perpendicular to the direction of the length 1404 of the conductive elements 1400 is kept low. According to various exemplary embodiments, the distance 1608 of the spacing can be adjusted to further vary the reflectivity of the first planar variable reflector 1600. According to one exemplary embodiment, the distance 1608 of the spacing is selected to be approximately equal or greater than the length 1404 of one of the conductive elements 1400 of the interconnections 1500.

The elongated conductive elements 1400 forming the interconnections 1500 of the first exemplary planar variable reflector 1600 are oriented in an x-axis direction 1612. For example, the elongated conductive elements 1400 are parallel to one another. The conductive elements 1400 and junction elements 1504 are supported by a support layer 1616. The conductive elements 1400 are positioned to cover a two-dimensional area of the surface of the support layer 1616. According to various exemplary embodiments, the support layer 1616 can be permeable to electromagnetic field. For example, the support layer 1616 is formed of a dielectric sheet or similar support structure. For example, the support layer 1616 is a dielectric material having a low dielectric permittivity. For example, the permittivity of the dielectric support layer 1616 is approximately equal to the permittivity of air. For example, the support layer 1616 is selected to be a thin layer.

A plurality of parallel combination conductive elements can be formed from the elongated conductive elements 1400 through the control of the junction elements 1504. It will be appreciated that according to various exemplary embodiments described herein, the length and/or the impedance (including impedance per unit length) of the combination conductive elements can be adjusted through control of the junction elements 1504.

Since the plurality of conductive elements cover a two-dimensional area, the combination conductive elements formed therefrom will also cover the two-dimensional area. Incident electromagnetic signal reaching the area will energize the combination conductive elements further creating scattered (reflected) electromagnetic signals. Accordingly, the plurality of conductive elements 1400 covering the support layer 316 acts a variable electromagnetic field reflecting surface.

Since each of the conductive elements 1400 are oriented in the x-axis direction 1612, combination conductive elements formed therefrom will be responsive to the directional components of incident electromagnetic signals that are aligned with the orientation of the conductive elements 1400 of the first planar variable reflector 1600. Accordingly, interconnections 1500 of conductive elements 1400 forms a directional reflector, herein referred to as a x-planar reflector 300. It will be appreciated that the x-planar reflector 300 can be used to isolate and reflect components of incident electromagnetic signals having an orientation or polarization that is aligned with x-axis direction 312.

Similarly, the second planar variable reflector 304 includes a plurality of interconnections 200 that are placed side by side. The interconnections 200 are spaced apart from one another by a distance 324.

For example, the distance 324 of the spacing between the side-by-side interconnections 200 of second planar variable reflector 304 is substantially greater than the width 112 and height 108 of the conductive elements 1400 of the interconnections 200. Accordingly, the strength of electromagnetic fields being reflected or scattered in a direction perpendicular to the direction of the length 104 of the conductive elements 1400 is kept low. According to various exemplary embodiments, the distance 324 of the spacing can be adjusted to further vary the reflectivity of the first planar variable reflector 300. According to one exemplary embodiment, the distance 324 of the spacing is selected to be approximately equal or greater than the length 104 of one of the conductive elements 1400 of the interconnections 200.

The elongated conductive elements 1400 forming the interconnections 200 of the second exemplary planar variable 304 are oriented in a y-axis direction 328. For example, the elongated conductive elements 1400 are parallel to one another. The conductive elements 1400 and junction elements 1504 are supported by a second support layer 332. The conductive elements 1400 are positioned to cover a two-dimensional area of the surface of the second support layer 332. According to various exemplary embodiments, the support layer 332 can be permeable to electromagnetic field. For example, the second support layer 332 is formed of a thin dielectric sheet or similar support structure. For example, the second support layer 332 is a dielectric material having a low dielectric permittivity. For example, the permittivity of the dielectric support layer 332 is approximately equal to the permittivity of air. For example, the support layer 332 is selected to be a thin layer. A plurality of parallel combination conductive elements can be formed from the elongated conductive elements 1400 through the control of the junction elements 1504. It will be appreciated that according to various exemplary embodiments described herein, the length and/or the impedance (including impedance per unit length) of the combination conductive elements can be adjusted through control of the junction elements 1504.

Since the plurality of conductive elements cover a two-dimensional area, the combination conductive elements formed therefrom will also cover the two-dimensional area. Incident electromagnetic signal reaching the area will energize the combination conductive elements further creating scattered (reflected) electromagnetic signals. Accordingly, the plurality of conductive elements 1400 covering the support layer 332 acts a variable reflecting surface for electromagnetic signals.

Since each of the conductive elements 1400 are oriented in the y-axis direction 328, combination conductive elements formed therefrom will be responsive to directional components of incident electromagnetic signals that are aligned with the orientation of the conductive elements 1400 of the second planar variable reflector 1604. Accordingly, interconnections 1500 of conductive elements 1400 forms a directional reflector, herein referred to as a y-planar reflector 1604. It will be appreciated that the y-planar reflector 1604 can be used to isolate and reflect incident electromagnetic signals having an orientation or polarization that is aligned with y-axis direction 1628.

Figure 20:
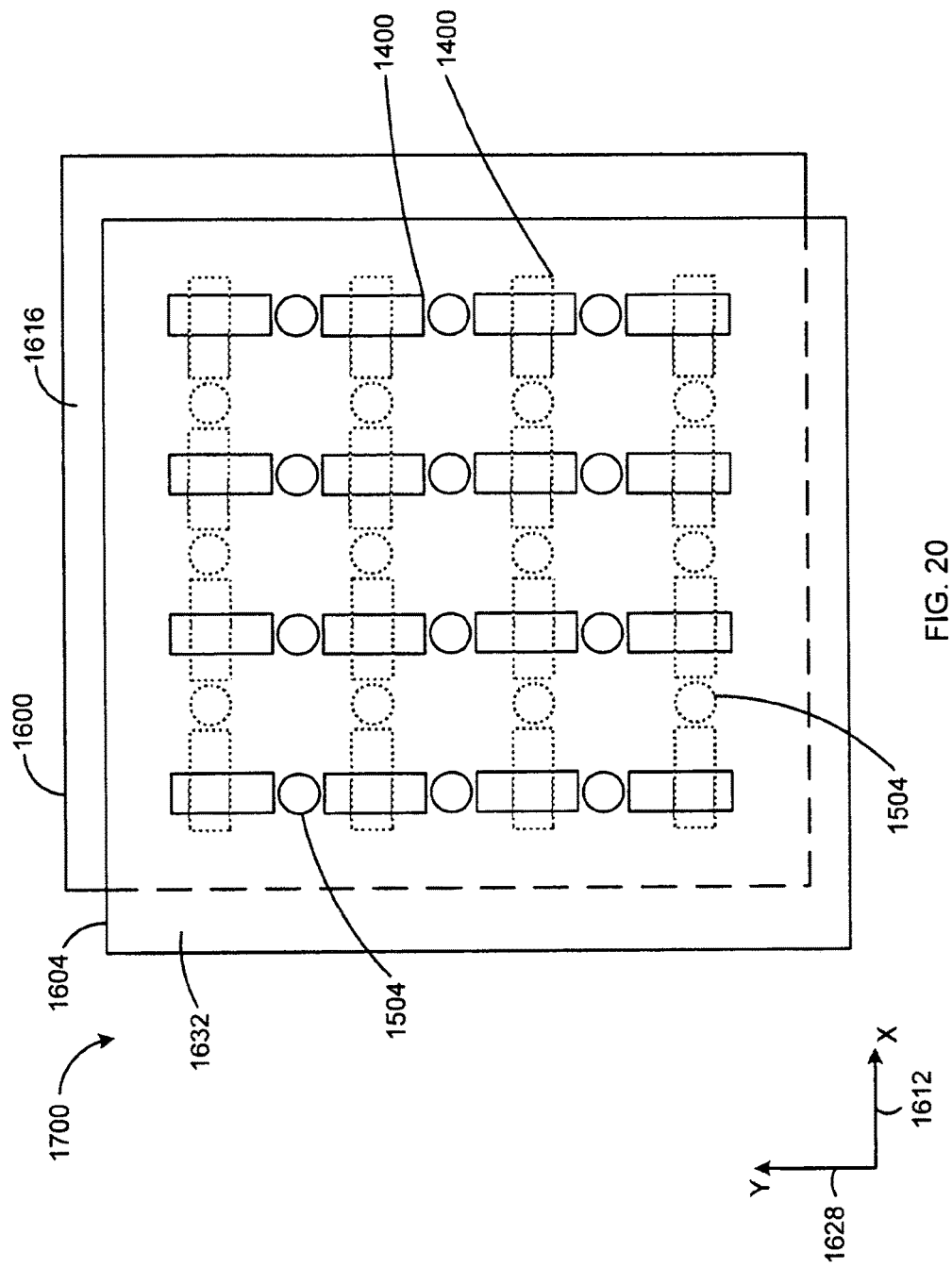
FIG. 20 illustrates a perspective view of a multi-directional variable reflector according to various exemplary embodiments.

Referring now to FIG. 20, therein illustrated is an exemplary multi-directional variable reflector 1700 formed by stacking a plurality of support layers 1616, 1632 having directionally oriented conductive elements 1400. As shown in FIG. 9, the y-planar reflector 1604 is positioned over the x-planar reflector 1600 such that the reflecting areas of the two reflectors 1600, 1604 are coincident. This coincidence can be seen from the corresponding positioning of conductive elements 1400 of the x-planar reflector 1600 with the conductive elements 1400 of the y-planar reflector 1604. The supporting layer 1632 of the y-planar reflector 1604 is permeable to electromagnetic signals. Accordingly, some of the incident electromagnetic signals reaching the y-planar reflector 1604 permeate through the supporting layer 1632 to reach the x-planar reflector 1600.

In addition to varying the length and the impedance of the combination conducting elements 1500 that act as reflecting elements, the multi-directional variable reflector 1700 is further operable to selectively vary a direction-dependent reflecting property of the reflector 1700 based on the control of the variable impedance junction elements 1504. For example, the reflector 1700 can be adjusted to selectively reflect directional components of incident electromagnetic signals aligned with only the x-axis direction 1612, only the y-axis direction 1628, or both directions.

For example, to adjust the multi-directional variable reflector 1700 to only reflect directional components of incident electromagnetic signals in the y-axis direction 1628, the variable impedance junction elements 1504 of the second support layer 1632 are controlled to have a high impedance such that the combination conducting elements formed from the conducting elements 1400 of the second support layer 1632 will have a high impedance per length. As a result, when y-axis direction oriented combination conducting elements of the second support layer 1632 are energized by the y-axis direction component of incident electromagnetic signals; the resulting current flow in the combination conductive elements will be low. Consequently, the scattered (reflected) electromagnetic signals from these combination conductive elements will also be low. By contrast, the junction elements 1504 of the first support layer 1616 are controlled to have lower impedance such that the combination conducting elements formed from the conducting elements 1400 of the first support layer 1616 will have lower impedance per length. As a result, when x-axis direction oriented combination conducting elements of the first support layer 1616 are energized by x-axis direction components of the incident electromagnetic signals; the resulting current flow in the combination conductive elements will be higher. Consequently, the scattered (reflected) electromagnetic signals from the combination conductive elements of the x-planar reflector 1604 will be high. Therefore the scattered electromagnetic signals emitted from the multi-direction variable reflector 700 will be due primarily to the energizing by the x-axis direction component of the incident electromagnetic signal. Measuring the scattered electromagnetic signals will allow a determination of properties of the x-axis component of the incident electromagnetic signals. It will be appreciated that the multi-directional variable reflector 1700 allows for determination of direction-dependent properties of the incident electromagnetic signal and/or space surrounding the reflector 1700. Furthermore, examining the scattered fields at a distance will provide an indication of one or more properties of the environment near the multi-directional variable reflector 1700 through which the waves having a given field orientation or polarization traveled because only waves with the given orientation or polarization impinging on the reflector 1700 will create a measurable response.

It will be understood that the multi-directional variable reflector 1700 is shown to have the y-planar reflector 1604 stacked above the x-planar reflector 1600 by way of example only and that various other combinations are possible. According to various exemplary embodiments, the x-planar reflector 1600 can be the top reflector and is stacked above the y-planar reflector 1604. According to various exemplary embodiments, the multi-directional variable reflector 1700 can be formed of more than two support layers having conductive elements supported thereon. For example, in addition to the x-planar reflector 1600 and y-planar reflector 1604, additional reflectors having conductive elements oriented in other directions may be added to the stacked reflectors.

Figure 21:
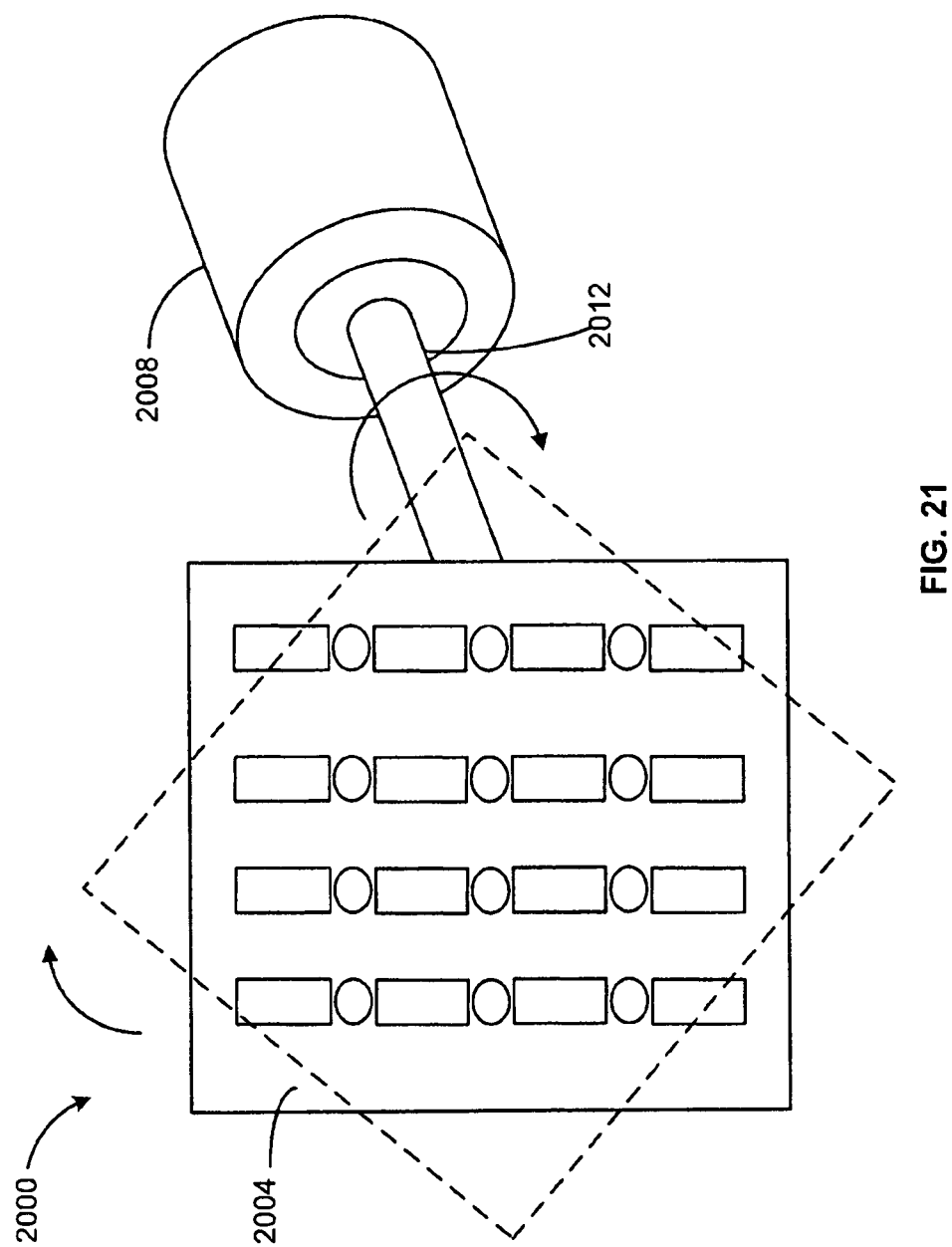
FIG. 21 illustrates a perspective view of a multi-directional variable reflector according to various exemplary embodiments.

Referring now to FIG. 21, therein illustrated is a perspective view according to various exemplary embodiments of a mechanically powered variable reflector 2000. A supporting layer 2004 having a plurality elongated conductive elements of the reflector 2000 is coupled to a motor 2008. For example, the variable reflector 2000 can be coupled to the motor via a shaft 2012. A plurality of elongated conductive elements 1400 and variable impedance junction elements 1504 are supported on the supporting layer 2004. For example, the elongated conductive elements 1400 and junction elements 1504 can be oriented in a similar manner to x-planar reflector 1600 or y-planar reflector 1604. With this embodiment both mechanical rotation and change in the connection between conducting elements can both be used to create the modified reflectivity either simultaneously or independently. A simple rotating object with elongated metal elements can be used to provide a very simple modulated reflector.

Rotating the supporting layer 2004 to a first position causes the conductive elements 1400 to be oriented in a first direction and for the variable reflector 2000 to isolate and reflect components of incident electromagnetic signals having an orientation or polarization that is aligned with the first direction. The supporting layer 2004 can be rotated about the shaft 2012 by the motor 2008 to a second position wherein the conductive elements 1400 are oriented in a second direction. In the second position, variable reflector 2000 isolates and reflects components of incident electromagnetic signals having an orientation or polarization that is aligned with the second direction. For example, rotating the supporting layer 2004 by an angle of 90 degrees causes the second direction to be orthogonal to the first direction. Through rotation of the supporting layer 2004 the reflector 2000 can be controlled to reflect different directional components of incident electromagnetic signals.

While exemplary embodiments described herein have linearly arranged conductive elements positioned on a planar support layer, it will be understood that other arrangements of conductive elements are possible. According to one exemplary embodiment, the conducting elements are curvilinear and are positioned on a curvilinear surface of a support layer.

According to one exemplary embodiment, electromagnetic simulation along with parameterization of the junction elements 1504 can be used to select appropriate sizing and positioning of the conductive elements 1400. In particular a systematic simulation of the response may be applied. Furthermore, modern computers and numerical simulation tools may be used to allow the optimization of the various parameters.

For example, by defining a design outcome in terms of scattered electromagnetic field strength, polarization change, range of frequencies, a wide range of electromagnetic modeling can be used to characterize the scattering of the incident field as a function of characteristics of the conductive elements 1400.

Iteratively adjustment of the parameters may be further carried out to achieve a desired response of the resulting reflector. For example, a manual succession of steps may include systematically adjusting the model parameters to achieve a desired response. Alternatively an automated process commonly referred to as inversion, which systematically modifies the model parameters with a goal of finding a set of parameters for the system that minimizes the difference between the desired response and the model response, may also be applied.

Figure 22:
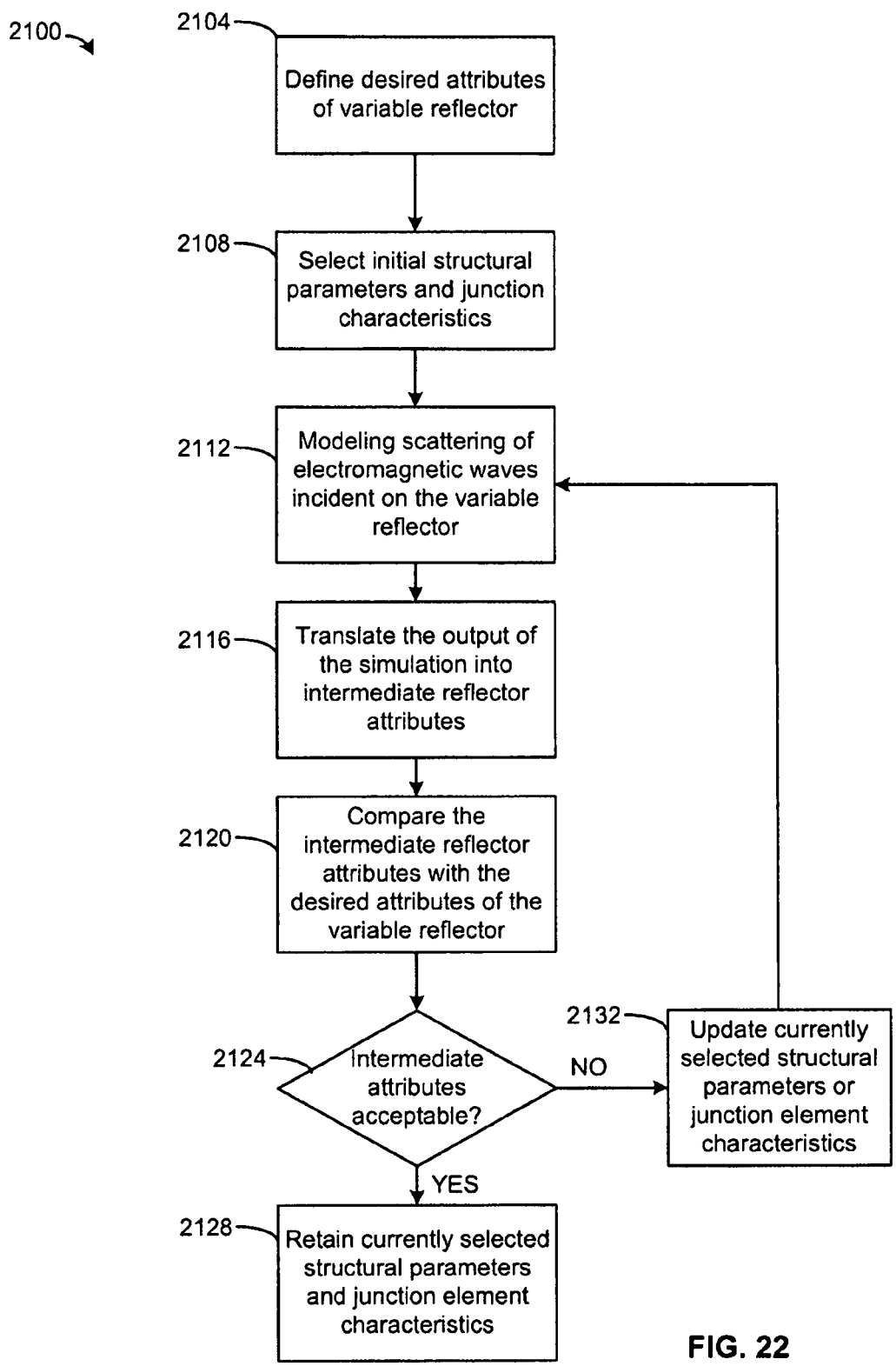
FIG. 22 illustrates a schematic diagram of an exemplary method for designing a variable reflector.

Referring now to FIG. 22, therein illustrated is a schematic diagram of a flowchart showing the steps of a method 2100 for adjusting the parameters of a reflector.

At step 2104, the desired attributes of the variable reflector is defined. For example it can be defined that the variable reflector should be capable of reflecting electromagnetic signals in a specific frequency range, of reflecting electromagnetic signals at a specific range of amplitudes (amplitude of the reflecting property of the reflector) or of reflecting electromagnetic signals having specific orientation or polarization.

At step 2108, initial structural parameters of the variable reflector are selected. For example, structural parameters can include one or more of the size of a reflecting surface defined by the conductive elements 1400, the spacing between interconnections 1500 of the reflecting surface, the length of each conductive element 1400, and the type of material forming the dielectric substrate of the variable reflector. Furthermore, initial characteristics of the junctions 1504 can also be selected. The initially selected structural parameters of the variable reflector and initial characteristics of the junctions 1504 are defined as currently selected structural parameters and junction element characteristics.

At step 2112, a simulation modeling of electromagnetic waves incident on the variable reflector is performed using the selected structure parameters and junction characteristics as inputs. The simulated scattered signal is outputted from the modeling.

At step 2116, the simulated scattered signal outputted from the modeling is translated into intermediate attributes of the variable reflector. For example, the intermediate attributes may be calculated based on a comparison of the input electromagnetic signals used in the simulation modeling with the outputted simulated scattered signal.

At step 2120, the intermediate attributes of the variable reflector are compared with the desired attributes of the variable reflector defined at step 2104.

At step 2124, it is determined based on the comparison of step 2120 whether the intermediate attributes of the variable reflector are acceptable. For example, it is determined whether the values of the intermediate attributes are sufficiently close to the values of the desired attributes of the variable reflector.

If at step 2124, the intermediate attributes are acceptable, the currently selected structural parameters and characteristics of the junction elements are retained at step 2128. A physical variable reflector can then be manufactured according to the retained structural parameters and junction element characteristics.

If at step 2124, the intermediate attributes are not acceptable, at least one of the currently selected structural parameters or junction element characteristics is updated at step 2132. For example, the updating may be based on an amount of difference between the intermediate attributes and the desired attributes of the variable reflector. For example, the updating of at least one of the selected structural parameters or junction element characteristics can use a perturbation approach known in the art. The updated structural parameters and junction element characteristics are defined as the currently selected structural parameters and junction element characteristics. The method returns to step 2112 to perform a further simulation modeling of electromagnetic waves incident on the variable reflector using the selected structure parameters and junction characteristics as inputs.

Advantageously, various exemplary embodiments described herein apply scattering principle to create a variable wideband reflector where the reflecting property can be adjusted through systematic control of junction elements. Such variable reflectors can be used to measure various properties of signals or conditions.

For example, where properties of the conducting elements and the surrounding space are known, measurement of the scattered electromagnetic field allows determination of properties of the incident electromagnetic signal. This can include frequency-related or orientation-related properties of the incident electromagnetic signal.

For example, where properties of the conducting elements and the incident electromagnetic signal are known, measurement of the scattered electromagnetic field allows determination of properties of environmental conditions in the space surrounding the reflector. For example, in the case of junction elements having impedance that varies with a changing environmental condition, measurement of the scattered electromagnetic field allows a determination of the impedance values of the junction elements, which provides a further indication of the environmental conditions. For example, where directional components of the incident electromagnetic signal are known, measurement of the scattered electromagnetic field allows a determination of direction-dependent properties of the environmental condition.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

REFERENCES

1. Kraus, J. D., 1988, Antennas, McGraw Hill, ISBN 0-07-035422-7
2. Aydin Babakhani, David B. Rutledge, and Ali Hajimiri, 2008, Transmitter Architectures Based on Near-Field Direct Antenna Modulation, IEEE JOURNAL OF SOLID-STATE CIRCUITS, VOL. 43, NO. 12
3. Brunfeldt, D. R., Ulaby, F. T., 1984 Active Reflector for Radar Calibration Geoscience and Remote Sensing, IEEE Transactions on, GE-22, Issue: 2
4. Foster I. J., 1998, Modulating Reflector Circuit, U.S. Pat. No. 5,822,685
5. Finkenzeller, K, 1999, RFID handbook: radio-frequency identification fundamentals and applications, John Wiley (New York) ISBN 0471988510
6. Shober, R. A., Sweetman, E, Wright, G. A., 2001, Inexpensive Modulated Backscatter Reflector, U.S. Pat. No. 6,243,012 B1
7. Bracht, R., Miller, E. K., Kuckertz, T., 1997, Using an impedance modulated reflector for passive communication, Antennas and Propagation Society International Symposium, 1997, IEEE, 1997 Digest, v2

The invention claimed is:

1. A system for measuring at least one physical property of a material, the system comprising:
   at least one transmitter configured to transmit at least a first signal and a second signal;
   at least one variable reflector configured to reflect a portion of the first signal to produce a first reflected signal, the portion of the first signal having traveled through the material, and configured to reflect a portion of the second signal to produce a second reflected signal, the portion of the second signal having traveled through the material;
   at least one receiver configured to receive at least a first received signal and at least a second received signal, the first received signal comprising the first reflected signal having traveled through the material and the second received signal comprising the second reflected signal having traveled through the material; and
   a processor in communication with the at least one receiver;

wherein the at least one variable reflector is configured to reflect the portion of the first signal with a reflecting property having a first reflecting property value;

the at least one variable reflector is configured to reflect the portion of the second signal with the reflecting property having a second reflecting property value that is different from the first reflecting property value;

the at least one variable reflector is adjustable to change the value of the reflecting property by adjusting a reflectivity of the at least one variable reflector; and the processor is configured to determine the at least one physical property of the material using the first received signal and the second received signal.

2. The system of claim 1, wherein the at least one transmitter is configured to transmit the first signal and the second signal temporally spaced apart.

3. The system of claim 2, wherein temporally spacing apart the transmitting of the first signal and the second signal permits independent observation of the first reflected signal and the second reflected signal.

4. The system of claim 1, wherein the first signal and second signal are the same.

5. The system of claim 1, wherein:

the processor is configured to isolate the first reflected signal and the second reflected signal, and determine at least one physical property of the material using the isolated reflected signals.

6. The system of claim 5, wherein the first received signal further comprises an unreflected portion of the first signal and the second received signal further comprises an unreflected portion of the second signal, and wherein the processor is configured to isolate the first reflected signal and the second reflected signal from the unreflected portion of the first signal and the unreflected portion of the second signal by calculating a difference between the first received signal and the second received signal.

7. The system of claim 1, wherein the at least one property of the material comprises the dielectric permittivity of the material.

8. The system of claim 1, wherein the at least one property of the material comprises the attenuation coefficient of the material.

9. The system of claim 1, wherein the at least one transmitter is configured to transmit the first signal as a transient pulse and the second signal as a transient pulse; and the processor is configured to determine a first time delay between transmitting the first signal and a corresponding pulse in the first received signal and a second time delay between transmitting the second signal and a corresponding pulse in the second received signal and to determine the at least one property of the material using the first time delay and the second time delay.

10. The system of claim 1, wherein the at least one transmitter is configured to transmit the first signal as a periodic signal and the second signal as a periodic signal having the same period as the first signal, and the processor is configured to determine a first phase delay between the first signal and the first received signal and a second phase delay between the second signal and the second received signal and to determine the at least one property of the material using the first phase delay and the second phase delay.

11. The system of claim 1, wherein the variable reflector is adjustable between a first directional reflectivity to reflect signals having a first polarization, and a second directional reflectivity to reflect signals having a second polarization;

and wherein the processor is further configured to determine the anisotropy of the material.

12. The system of claim 11, wherein the first polarization and the second polarization are orthogonal.

13. The system of claim 12, wherein the first reflecting property value and the second reflecting property value are direction-independent.

14. The system of claim 1, wherein the at least one transmitter is configured to transmit the first signal with a first polarization and to transmit the second signal with a second polarization, and the processor is further configured to determine an anisotropy of the material.

15. The system of claim 14, wherein the first polarization and the second polarization are orthogonal.

16. The system of claim 1, wherein the at least one transmitter is configured to transmit the first signal in a first frequency range and to transmit the second signal in a second frequency range;

the first reflecting property value is a reflectivity for the first frequency range and the second reflecting property value is a reflectivity for the second frequency range; and the processor is configured to determine frequency dependent properties of the material.

17. The system of claim 1, wherein the first signal has a differentiable amplitude in a first frequency range and the second signal has a differentiable amplitude in a second frequency range, and wherein at least one property of the material includes frequency dependent properties of the material.

18. The system of claim 1, further comprising a controller configured to select the value of the reflecting property of the variable reflector.

19. The system of claim 18, wherein the second signal is transmitted after the first signal, and wherein the controller is configured to select the first reflecting property value before the variable reflector reflects the portion of the first signal and to select the second reflecting property value before the variable reflector reflects the portion of the second signal.

20. A system for measuring a material, the system comprising:

at least one transmitter for transmitting at least a first signal and a second signal;

at least one variable reflector for reflecting a portion of the first signal at a first reflecting property to produce a first reflected signal, the portion of the first signal having traveled through the material, and for reflecting a portion of the second signal at a second reflecting property to produce a second reflected signal, the portion of the second signal having traveled through the material;

at least one receiver for receiving at least a first received signal and at least a second received signal, the first received signal comprising the first reflected signal having traveled through the material and the second received signal comprising the second reflected signal having traveled through the material, the first reflected signal and the second reflected signal providing an indication of at least one property of the material; and a controller for selecting a reflecting property of the variable reflector;

wherein the transmitter sequentially transmits a plurality of signals; and wherein the variable reflector reflects a first subset of the plurality of signals at the first reflecting property and reflects a second subset of the plurality of signals at the second reflecting property;

wherein the controller adjusts the reflecting property of the variable reflector during the transmission of the plurality of signals.

21. The material measurement system of claim 20, wherein the controller adjusts the reflecting property of the variable reflector independently of the timing of the sequential transmissions of the plurality of signals.

22. A method for measuring a material, the method comprising:

transmitting at least a first signal into the material and a second signal into the material;

controlling at least one reflector to reflect a portion of the first signal at a first reflecting property to produce a first reflected signal, the portion of the first signal having traveled through the material;

controlling the at least one reflector to reflect a portion of the second signal at a second reflecting property to produce a second reflected signal, the portion of the second signal having traveled through the material;

receiving at least a first received signal and at least a second received signal, the first received signal comprising the first reflected signal having traveled through the material and the second received signal comprising the second reflected signal having traveled through the material, the first reflected signal and the second reflected signal providing an indication of at least one property of the material.

* * * * *